US008552054B2

(12) United States Patent
Swindell et al.

(10) Patent No.: US 8,552,054 B2
(45) Date of Patent: *Oct. 8, 2013

(54) FATTY AMINE DRUG CONJUGATES

(75) Inventors: Charles S. Swindell, Merion, PA (US); Glenn J. Fegley, Eagleville, PA (US)

(73) Assignee: Luitpold Pharmaceuticals, Inc., Shirley, NY (US)

( * ) Notice: Subject to any disclaimer, the term of this patent is extended or adjusted under 35 U.S.C. 154(b) by 981 days.

This patent is subject to a terminal disclaimer.

(21) Appl. No.: 10/108,255

(22) Filed: Mar. 25, 2002

(65) Prior Publication Data

US 2003/0065023 A1   Apr. 3, 2003

Related U.S. Application Data

(60) Provisional application No. 60/278,552, filed on Mar. 23, 2001.

(51) Int. Cl.
*A61K 31/337* (2006.01)
*C07D 305/14* (2006.01)

(52) U.S. Cl.
USPC ............................ 514/449; 549/510; 549/511

(58) Field of Classification Search
USPC ................................... 549/510, 511; 514/449
See application file for complete search history.

(56) References Cited

U.S. PATENT DOCUMENTS

| | | |
|---|---|---|
| 3,539,573 A | 11/1970 | Schmutz |
| 3,621,048 A | 11/1971 | Bauman |
| 3,646,201 A | 2/1972 | Kallianos et al. |
| 4,088,646 A | 5/1978 | Ishida et al. |
| 4,097,597 A | 6/1978 | Horrom et al. |
| 4,185,095 A | 1/1980 | Young |
| 4,218,234 A | 8/1980 | Nadasy et al. |
| 4,287,184 A | 9/1981 | Young |
| 4,346,085 A | 8/1982 | Growdon et al. |
| 4,351,831 A | 9/1982 | Growden et al. |
| 4,407,744 A | 10/1983 | Young |
| 4,550,109 A | 10/1985 | Folkers et al. |
| 4,554,272 A | 11/1985 | Bock et al. |
| 4,558,049 A | 12/1985 | Bernardi et al. |
| 4,636,494 A | 1/1987 | Growdon et al. |
| 4,684,646 A | 8/1987 | Chang et al. |
| 4,692,441 A | 9/1987 | Alexander et al. |
| 4,704,393 A | 11/1987 | Wakabayashi et al. |
| 4,729,989 A | 3/1988 | Alexander |
| 4,788,063 A | 11/1988 | Fisher et al. |
| 4,814,470 A | 3/1989 | Colin et al. |
| 4,857,653 A | 8/1989 | Colin et al. |
| 4,868,161 A | 9/1989 | Roberts |
| 4,902,505 A | 2/1990 | Pardridge et al. |
| 4,933,324 A | 6/1990 | Shashoua |
| 4,939,174 A | 7/1990 | Shashoua |
| 4,943,579 A | 7/1990 | Vishnuvajjala et al. |
| 4,968,672 A | 11/1990 | Jacobson et al. |
| 5,059,699 A | 10/1991 | Kingston et al. |
| 5,068,224 A | 11/1991 | Fryklund et al. |
| 5,112,596 A | 5/1992 | Malfroy-Camine |
| 5,112,863 A | 5/1992 | Hashimoto et al. |
| 5,116,624 A | 5/1992 | Horrobin et al. |
| 5,120,760 A | 6/1992 | Horrobin |
| 5,141,958 A | 8/1992 | Crozier-Willi et al. |
| 5,169,762 A | 12/1992 | Gray et al. |
| 5,169,764 A | 12/1992 | Shooter et al. |
| 5,194,654 A | 3/1993 | Hostetler et al. |
| 5,214,062 A | 5/1993 | Mark et al. |
| 5,216,023 A | 6/1993 | Literati et al. |
| 5,216,142 A | 6/1993 | Horrobin et al. |
| 5,223,263 A | 6/1993 | Hostetler et al. |
| 5,246,726 A | 9/1993 | Horrobin et al. |
| 5,250,722 A | 10/1993 | Bombardelli et al. |
| 5,276,020 A | 1/1994 | Horrobin et al. |
| 5,278,324 A | 1/1994 | Kingston et al. |
| 5,284,876 A | 2/1994 | Shashoua |
| 5,308,832 A | 5/1994 | Garleb et al. |
| 5,314,991 A | 5/1994 | Oka et al. |
| 5,336,684 A | 8/1994 | Murray et al. |
| 5,352,596 A | 10/1994 | Cheung et al. |
| 5,356,928 A | 10/1994 | Murray et al. |
| 5,362,831 A | 11/1994 | Mongelli et al. |
| 5,411,947 A | 5/1995 | Hostetler et al. |
| 5,420,276 A | 5/1995 | Norbeck |
| 5,447,936 A | 9/1995 | Hausheer et al. |

(Continued)

FOREIGN PATENT DOCUMENTS

AU    746472    6/1999
AU    770519    4/2001

(Continued)

OTHER PUBLICATIONS

Franciscus M. H. de Groot, Leon W. A. van Berkom, and Hans W. Scheeren, Synthesis and biological Evaluation of 2'-Carbamate-Linked and 2'-Carbonate-Linked Prodrugs of Paclitaxel: Selective Activation by the Tumor-Associated Protease Plasmin, J. Med. Chem. 43:3093-3102 (2000).*
C. John Blankley, Lawrence R. Bennett, Robert W. Fleming, Ronald D. Smith, Deirdre K. Tessman, and Harvey R. Kaplan, Antihypertensive Activity of 6-Arylpyrido[2,3-d]pyrimidin-7-amine Derivatives. 2. 7-Acyl Amide Analogues, J. Med. Chem, 26:403-411 (1983).*
Haymach et al., Epidermal growth factor receptor inhibitors in development for the treatment of non-small cell lung cancer, Clin. Cancer. Res. Jul. 15, 2006;12(14 Pt 2):4441s-4445s.*
Exhibit I.*
Mayhew et al. "Hydrophobic taxane . . . " CA 126:84589 (1996).*
Webb et al. "Fatty acid . . . " CA 133:232814 92000).*
Pike et al. "Nutrition . . . "p. 29-30 (1984).*
Bundgaard "Design of prodrugs" p. 1, 6-7 (1985).*
Groot et al. "Synthesis and . . . " J. Med. Chem. v.43 p. 3093-3102 (2000).*

(Continued)

Primary Examiner — Celia Chang
(74) Attorney, Agent, or Firm — Wolf, Greenfield & Sacks, P.C.

(57) ABSTRACT

The invention provides conjugates of fatty amines and pharmaceutical agents useful in treating cancer, viruses, psychiatric disorders. Compositions, pharmaceutical preparations, and methods of preparations of the fatty amine-pharmaceutical agent conjugates are provided.

15 Claims, No Drawings

(56) References Cited

U.S. PATENT DOCUMENTS

| | | |
|---|---|---|
| 5,453,520 A | 9/1995 | Bombardelli et al. |
| 5,453,521 A | 9/1995 | Gaullier et al. |
| 5,459,256 A | 10/1995 | Marquez et al. |
| 5,466,841 A | 11/1995 | Horrobin et al. |
| 5,468,754 A | 11/1995 | Hausheer et al. |
| 5,473,055 A | 12/1995 | Mongelli et al. |
| 5,476,954 A | 12/1995 | Bourzat et al. |
| 5,484,809 A | 1/1996 | Hostetler et al. |
| 5,494,999 A | 2/1996 | Hale et al. |
| 5,496,714 A | 3/1996 | Comb et al. |
| 5,504,102 A | 4/1996 | Agharkar et al. |
| 5,516,800 A | 5/1996 | Horrobin |
| 5,532,372 A | 7/1996 | Saji et al. |
| 5,532,374 A | 7/1996 | Lee et al. |
| 5,534,499 A | 7/1996 | Ansell |
| 5,545,719 A | 8/1996 | Shashoua |
| 5,580,556 A | 12/1996 | Horribin |
| 5,580,899 A | 12/1996 | Mayhew et al. |
| 5,597,719 A | 1/1997 | Freed et al. |
| 5,603,959 A | 2/1997 | Horrobin et al. |
| 5,604,198 A | 2/1997 | Poduslo et al. |
| 5,604,216 A | 2/1997 | Horrobin |
| 5,646,180 A | 7/1997 | Chaturvedi |
| 5,654,290 A | 8/1997 | Bayon et al. |
| 5,716,614 A | 2/1998 | Katz et al. |
| 5,750,572 A | 5/1998 | Bruzzese |
| 5,795,909 A * | 8/1998 | Shashoua et al. ............. 514/449 |
| 5,814,456 A | 9/1998 | O'Rand et al. |
| 5,824,701 A | 10/1998 | Greenwald et al. |
| 5,827,819 A | 10/1998 | Yatvin et al. |
| 5,919,815 A | 7/1999 | Bradley et al. |
| 5,922,695 A | 7/1999 | Arimilli et al. |
| 5,925,669 A | 7/1999 | Katz et al. |
| 5,955,459 A | 9/1999 | Bradley et al. |
| 5,977,061 A | 11/1999 | Holy et al. |
| 5,977,089 A | 11/1999 | Arimilli et al. |
| 5,977,174 A | 11/1999 | Bradley et al. |
| 5,985,854 A | 11/1999 | Kozak |
| 5,994,392 A | 11/1999 | Shashoua |
| 6,005,004 A | 12/1999 | Katz et al. |
| 6,024,977 A | 2/2000 | Yatvin et al. |
| 6,043,230 A | 3/2000 | Arimilli et al. |
| 6,069,249 A | 5/2000 | Arimilli et al. |
| 6,077,837 A | 6/2000 | Kozak |
| 6,080,877 A | 6/2000 | Swindell et al. |
| 6,107,499 A | 8/2000 | Shashoua |
| 6,136,796 A | 10/2000 | Kozak |
| 6,153,653 A | 11/2000 | Shashoua |
| 6,166,089 A | 12/2000 | Kozak |
| 6,197,764 B1 | 3/2001 | Bradley et al. |
| 6,225,444 B1 | 5/2001 | Shashoua |
| 6,225,460 B1 | 5/2001 | Bischofberger et al. |
| 6,245,811 B1 | 6/2001 | Horrobin et al. |
| 6,252,060 B1 | 6/2001 | Hostetler |
| 6,258,836 B1 | 7/2001 | Shashoua |
| 6,281,376 B1 | 8/2001 | Whittaker et al. |
| 6,291,690 B1 | 9/2001 | Mayhew et al. |
| 6,384,019 B1 | 5/2002 | Myhren et al. |
| 6,407,075 B1 | 6/2002 | Scott et al. |
| 6,407,137 B2 | 6/2002 | Shashoua |
| 6,448,392 B1 | 9/2002 | Hostetler et al. |
| 6,555,700 B1 | 4/2003 | Horrobin et al. |
| 6,576,636 B2 | 6/2003 | Webb et al. |
| 6,602,902 B2 | 8/2003 | Shashoua et al. |
| 6,627,601 B2 | 9/2003 | Shashoua |
| 7,235,583 B1 | 6/2007 | Webb et al. |
| 7,816,398 B2 | 10/2010 | Swindell et al. |
| 8,314,077 B2 | 11/2012 | Webb et al. |
| 2001/0006962 A1 | 7/2001 | Myhren et al. |
| 2004/0106589 A1 | 6/2004 | Webb et al. |
| 2008/0090803 A1 | 4/2008 | Swindell et al. |
| 2008/0125380 A1 | 5/2008 | Webb et al. |
| 2008/0153899 A1 | 6/2008 | Swindell et al. |
| 2012/0148595 A1 | 6/2012 | Swindell et al. |

FOREIGN PATENT DOCUMENTS

| | | |
|---|---|---|
| DE | 24 56 947 A1 | 6/1975 |
| DE | 260 2175 | 7/1976 |
| DE | 29 32 869 A1 | 2/1980 |
| DE | 422 4737 | 2/1994 |
| EP | 0 030 009 A1 | 6/1981 |
| EP | 0 035 375 A1 | 9/1981 |
| EP | 0 091 694 A1 | 10/1983 |
| EP | 0 311 100 A2 | 4/1989 |
| EP | 0 350 287 | 10/1990 |
| EP | 0 599 576 A1 | 1/1994 |
| EP | 0 615 752 A1 | 9/1994 |
| EP | 0 693 498 A1 | 1/1996 |
| EP | 0 761 644 A | 3/1997 |
| EP | 0909183 B1 | 8/2004 |
| FR | 2.165.760 | 8/1973 |
| FR | 2 592 883 A | 7/1987 |
| FR | 2 698 269 A | 8/1997 |
| GB | 2296239 * | 6/1996 |
| JP | 75-9469 | 1/1975 |
| JP | 55053208 A | 4/1980 |
| JP | 75-427/1983 | 4/1983 |
| JP | 59025327 A | 2/1984 |
| JP | 59-204175 | 11/1984 |
| JP | 61204136 | 11/1984 |
| JP | 1153629 A | 6/1989 |
| JP | 1203331 A | 8/1989 |
| JP | 1287022 A | 11/1989 |
| JP | 2256624 A | 10/1990 |
| JP | 6016548 A | 1/1994 |
| JP | 6072868 | 3/1994 |
| JP | H06-501939 | 3/1994 |
| JP | 7082146 | 3/1995 |
| JP | 8027010 A | 1/1996 |
| JP | 8151334 | 6/1996 |
| JP | 8163991 A | 6/1996 |
| JP | 8245378 A | 9/1996 |
| JP | 9025231 A | 1/1997 |
| JP | 9030963 | 2/1997 |
| JP | 11-504914 | 5/1998 |
| JP | 10168047 A | 6/1998 |
| JP | 2001-522351 | 11/2001 |
| SU | 477159 A | 10/1976 |
| WO | WO 85/00520 | 2/1985 |
| WO | WO 89/02733 | 4/1989 |
| WO | WO 89/07938 | 9/1989 |
| WO | WO 90/00555 | 1/1990 |
| WO | WO 92/06089 | 4/1992 |
| WO | WO 92/06089 A | 4/1992 |
| WO | WO 92/16554 | 10/1992 |
| WO | WO 92/20362 | 11/1992 |
| WO | WO 93/00910 | 1/1993 |
| WO | WO 93/11668 | 6/1993 |
| WO | WO 94/07880 | 4/1994 |
| WO | WO 94/11547 | 5/1994 |
| WO | WO 94/12530 | 6/1994 |
| WO | WO 94/13654 | 6/1994 |
| WO | WO 94/20089 | 9/1994 |
| WO | WO 94/22887 | 10/1994 |
| WO | WO 94/24107 | 10/1994 |
| WO | WO 95/01969 | 1/1995 |
| WO | WO 95/13270 | 5/1995 |
| WO | WO 95/13271 | 5/1995 |
| WO | WO 95/33736 | 12/1995 |
| WO | WO 96/01259 | 1/1996 |
| WO | WO 96/04001 | 2/1996 |
| WO | WO 96/12696 | 5/1996 |
| WO | WO 96/14308 | 5/1996 |
| WO | WO 96/14309 | 5/1996 |
| WO | WO 96/22303 | 7/1996 |
| WO | WO 96/27380 | 9/1996 |
| WO | WO 96/34855 | 11/1996 |
| WO | WO 96/34858 | 11/1996 |
| WO | WO 97/33173 A | 9/1997 |
| WO | WO 97/44026 | 11/1997 |
| WO | WO 97/44063 | 11/1997 |
| WO | WO 97/44336 | 11/1997 |
| WO | WO 98/09621 | 4/1998 |

(56) References Cited

FOREIGN PATENT DOCUMENTS

| | | |
|---|---|---|
| WO | WO 98/17325 | 4/1998 |
| WO | WO 98/21223 | 5/1998 |
| WO | WO 98/32718 | 7/1998 |
| WO | WO 98/32718 A | 7/1998 |
| WO | WO 98/43994 A | 10/1998 |
| WO | WO 99/02733 | 1/1999 |
| WO | WO 99/26620 | 6/1999 |
| WO | WO 99/44600 | 9/1999 |
| WO | WO 99/52887 | 10/1999 |
| WO | WO 00/01417 | 1/2000 |
| WO | WO 00/53231 | 9/2000 |
| WO | WO 01/62085 A1 | 8/2001 |
| WO | WO 00/53231 | 9/2002 |
| WO | WO 00/67802 | 11/2002 |
| WO | WO 02/087586 A1 | 11/2002 |
| ZA | 9603433 A | 10/1996 |

OTHER PUBLICATIONS

Buckley et al. "Preparation of carbamyl . . . " CA40:9942 (1946).*
Hardy et al. "Organic clay . . . " CA 53:86810 (1959).*
Fatty amine definition (2009) one page from internet.*
PCT/GB97/02362—Scotia Holdings, PLC—Search Report—Feb. 20, 1998.
PCT/GB99/00563—Scotia Holdings, PLC—Search Report—Aug. 19, 1999.
PCT/US89/00757—Shashoua—Search Report—Jun. 14, 1989.
PCT/US91/03346—Shashoua—Search Report—Sep. 6, 1991.
PCT/US97/08792—Neuromedica, Inc.—Search Report—Oct. 28, 1997.
PCT/US97/08866—Neuromedica, Inc.—Search Report—Sep. 3, 1997.
PCT/US97/08867—Neuromedica, Inc.—Search Report—Jan. 9, 1998.
PCT/US98/24412—Neuromedica, Inc.—Search Report—Feb. 22, 1999.
PCT/US98/24421—Neuromedica, Inc.—Search Report—Mar. 3, 1999.
PCT/US98/24490—Neuromedica, Inc.—Search Report—Feb. 26, 1999.
PCT/US99/01786—Neuromedica, Inc.—Search Report—Jul. 6, 1999.
PCT/US00/06160—Protarga, Inc.—Search Report—Oct. 4, 2001.
PCT/US00/12752—Protarga, Inc.—Search Report—Oct. 31, 2000.
Althaus, I.W. et al., "The amphiphilic properties of novenamines determine their activity as inhibitors of HIV-1 RNase H," *Experientia*, vol. 52, 1996, pp. 329-335, XP008039697.
Database Beilstein, *Beilstein Institute for Organic Chemistry*, Frankfurt-Main, DE, Jun. 29, 1989, XP002311506, Database accession No. 2146750 (BRN).
Database Beilstein, *Beilstein Institute for Organic Chemistry*, Frankfurt-Main, DE, Feb. 15, 1990, XP002311507, Database accession No. 3166362 (BRN).
Database Beilstein, *Beilstein Institute for Organic Chemistry*, Frankfurt-Main, DE, Jun. 29, 1989, XP002311508, Database accession No. 2270240 (BRN).
Database HCAPLUS ACS, Sep. 6, 1991, XP002311505, retrieved from STN, Database accession No. 115:91935/DN, RN 2411-58-7, 135346-35-9, 7418-03-3.
Guillonneau, C. et al., "Synthesis of 9-O-Substituted Derivatives of 9-Hydroxy-5,6-dimethyl-6H-pyrido[4,3-b]carbazole-1-carboxylic Acid (2-(Dimethylamino)ethyl)amide and Their 10- and 11-Methyl Analogues with Improved Antitumor Activity," *J. Med. Chem.* 1999, 42, pp. 2191-2203, XP002311501.
Hong, C.I. et al., "Synthesis and Biological Activity of $N^6$-(n-Alkylureido)purine Ribonucleosides and Their 5'-Phosphates," *J. Pharm. Sci.*, vol. 67, No. 4, Apr. 1978, pp. 569-571, XP008039688.
Kristian et al., "Isothiocyanates and Their Synthetic Producers. X. Synthesis of 3-Substituted 2-Thioxo-4-Oxo-3,4-Dihydro-2H-1,3-Benzoxazines," *Collect. Czech. Chem. Commun.*, vol. 37, 1972, pp. 2972-2974.
Lee, Heejoo et al., "Syntheses of 5-Fluorouracil-Fat Conjugates and Evaluation of Their in vitro Cytotoxic Activity." *Yakhak Hoechi*, vol. 34, 1990. pp. 395-400.
Lennartz, *Chem. Ber.*, vol. 75, 1942. pp. 833-842.
Liu, J. et al., "New Approaches for the Preparation of Hydrophobic Heparin Derivatives," *J. of Pharmaceutical Sciences*, vol. 83, No. 7, Jul. 1994, pp. 1034-1039, XP008038024.
Meyer, K. L. et al., "In Vitro Evaluation of Phosphocholine and Quaternary Ammonium Containing Lipids as Novel Anti-HIV Agents," *J. Med. Chem.* 1991, 34, pp. 1377-1383, XP002311504.
Ponpipom, M.M. et al., "Structure-Activity Relationships of C1 and C6 Side Chains of Zaragozic Acid A Derivatives," *J. Med. Chem* 1994, 37. pp. 4031-4051. XP-002311499.
Puglisi, G. et al., "Synthesis of Methotrexate $\alpha,\gamma$-Bis(Amides) and Correlation of Thermotropic and DPPC Biomembrane Interaction Parameters with Their Anticancer Activity," *Drug Development Research* 44, pp. 62-69 (1998), XP008039189.
Roark, W. H. et al., "Inhibitors of Acyl-CoA:Cholesterol Acyltransferase (ACAT). 2. Modification of Fatty Acid Anilide ACAT Inhibitors: Bioisosteric Replacement of the Amide Bond," *J. Med. Chem.* 1993, 36, pp. 1662-1668, XP002924002.
Sasse, A. et al., "Development of Chiral N-Alkylcarbamates as New Leads for Potent and Selective $H_3$-Receptor Antagonists: Synthesis, Capillary Electrophoresis, and in Vitro and Oral in Vivo Activity," *J. Med. Chem.* 1999, 42, pp. 593-600, XP-002311502.
Sergheraert, C. et al., "Synthesis and Anti-HIV Evaluation of D4T and D4T 5'-Monophosphate Prodrugs," *J. Med. Chem.* 1993, 36, pp. 826-830, XP-002311498.
Simoni, D. et al., "Geiparvarin Analogues. 2. Synthesis and Cytostatic Activity of 5-(4-Arylbutadienyl)-3(2H)-furanones and of N-Substituted 3-(4-Oxo-2-furanyl)-2-buten-2-yl Carbamates," *J. Med. Chem.* 1991, 34, pp. 3172-3176, XP-002311503.
Tanaka, T. et al., "Synthesis and Antioxidant Activity of Novel Amphipathic Derivatives of Tea Polyphenol," *Bioorganic & Medicinal Chemistry Letters* 8 (1998), pp. 1801-1806.
Tsushima, S. et al., "Syntheses and Biological Activities of N-Alkyl- and N-Alkenylcarbamoyl Phospholipids," *Chem. Pharm. Bull.* 32(7): pp. 2700-2713 (1984), XP-002311500.
Washburne, S. S. et al., "Isocyanates Derived from Fatty Acids by the Trimethylsilyl Azide Modification of the Curtius Rearrangement," *Journal of the American Oil Chemists' Society*, American Oil Chemists' Society, Champaign, U.S., vol. 49, 1972, pp. 694-695, XP008039249.
Supplementary Partial European Search Report in Application No. PCT/US02/09389, mailed Jan. 5, 2005.
Brutovska, A. et al., "Isothiocyanates and Their Synthetic Producers. VIII. The Synthesis and the Study of Spectral Features of Substituted Monothiourethanes," *Chem. Zvesti*, vol. 23, 1969, pp. 736-741.
International Search Report in PCT/US02/09389, mailed Feb. 10, 2004.
Wakselman et al., Anti-tumor protection induced in mice by fatty acid conjugates: alkyl butyrates and poly(ethylene glycol) dibutyrates. Int J Cancer. Sep. 15, 1990;46(3):462-7.
[No Author Listed], Drug metabolism. Burger's Medicinal Chemistry and Drug Delivery. $5^{th}$ Edition. vol. I: Principles and Practice. Ed. Wolff. John Wiley & Sons. 1995: pp. 171-174.
[No Author Listed], Fatty amines. Ullmann's Encyclopedia of Industrial Chemistry. Eds. Gerhartz et al. VCH Verlagsgesellschaft, Weinheim. 1985; $5^{th}$ Edition: vol. A 2; p. 18.
Brockmann et al., Fatty acids. Ullmann's Encyclopedia of Industrial Chemistry. Eds. Gerhartz et al. VCH Verlagsgesellschaft, Weinheim. 1987; $5^{th}$ Edition: vol. A 10; pp. 245-255.
Riemenschneider, Carboxylic acids, aliphatic. Ullmann's Encyclopedia of Industrial Chemistry. Eds. Gerhartz et al. VCH Verlagsgesellschaft, Weinheim. 1986; $5^{th}$ Edition: vol. A 5; pp. 235-248.
[No author listed], Dexamethasone palmitate: Chemical teratogens, carcinogens, mutagens. Hazard Database. CAS# [33755-46-3] ACX# [11012259]. Retrieved from http://www.evol.nw.ru/labs/lab38/spirov/hazard/dexamethasone_palmitate.html on Aug. 31, 2004.
Dischino et al., Synthesis of the monosodium salt of carbon-14 labeled paclitaxel (Taxol®) 2'-ethyl carbonate

(56) References Cited

OTHER PUBLICATIONS 7-phosphonooxymethyl ether, a potential prodrug of paclitaxel. J Labelled Compounds Radiopharmaceuticals. Feb. 1997;39(2):173-9. Epub Dec. 4, 2008.

Ansari, et al. "Fatty acid conjugates of xenobiotics" *Toxicology Letters* (1995)75:1-17.

Anel, A., et al., "Increased Cytotoxicity of Polyunsaturated Fatty Acids on Human Tumoral B and and T-Cell Lines Compared With Normal Lymphocytes", *Leukemia*, (1992), 6(7):680-688.

Anel, B., et al. "Cytotoxicity of Chlorambucil and Chlorambucil-Fatty Acid Conjugates Against Human Lymphomas and Normal Human Peripheral Blood Lymphocytes", *Biochem Pharmacol*,(1990),40(6):1193-1200.

Baldessarini, et al., "Dopamine and Pathophysiology of Dyskinesis . . . ", Ann. Rev. Neurosci. 3:23-41 (1980).

Begin, M.E., et al., "Differential Killing of Human Carcinoma Cells Supplemented With N-3 and N-6 Polyunsaturated Fatty Acids", *J Natl Cancer Inst*, (1986), 77(5):1053-1062. (Abstract).

Bourat, et al., "Long Chain Esters of Pipotiazine as Long-Acting Psychotropic Pro-Drug", *Med. Chem. Proc. Int. Symp.* 5th (1976) pp. 105-114.

Braam, J., et al., "Rain-, Wind-, and Touch-Induced Expression of Calmodulin and Calmodulin-Related Genes in Arabidopsis", *Cell*, 60"357-364 (1990).

Bridges, A.J. et al., "$N^6$-(2,2-Diphenylethyl)adenosine, a Novel Adenosine Receptor Agonist with Antipsychotic-like Activity", J. Med. Chem. 30:1709-1711 (1987).

Burns, C.P., et al., "Effect of Docosahexaenoic Acid on Rate of Differentiation of H1-60 Human Leukemia", *Cancer Res*, (1989), 49:3252-3258.

Carboni et al., "Synthesis of a Photoaffinity Analog of Taxol as an Approach to Identify the Taxol Binding Site on Microtubules", *Journal of Medicinal Chem.* (Sep. 8, 1992).

Chajes, V., et al., "Influence of N-3 Fatty Acids on the Growth of Human Breast Cancer Cells in Vitro: Relationship to Peroxides and Vitamin-E", *Breast Cancer Res Treat*, (1995), 34:199-212.

Chen, et al. "Taxol Structure-Activity Relationships: Synthesis and Biological Evaluation of Taxol Analogs Modified at C-7," *Bioorganic & Medicinal Chemistry Letters*, vol. 4, No. 18, pp. 2223-2228, 1994.

De Antueno, R.J., et al., "In Vitro Effect of Eicosapentaenoic and Docosahexaenoic Acids on Prostaglandin E2 Synthesis in a Human Lung Carcinoma", *Biochem Int*, (1989), 19(3):489-496. (Abstract).

De Groot, et al., "Synthesis and Biological Evaluation of 2'-Carbamate-Linked and 2'Carbonate-Linked Prodrugs of Paclitaxel: Selective Activation by the Tumor-Associated Protease Plasmin," *J. Med. Chem.*, 2000, vol. 43, pp. 3093-3102.

De Smidt, P.C., et al., "Characteristics of Association of Oleoyl Derivatives of 5-Fluorodeoxy-Uridine and Methotrexate With Low-Density Lipoproteins (Ldl)", *Pharm Res*, (1992), 9(4):565-569.

Deutsch, H.F., et al.,"Cytotoxic Effects of Daunomycin-Fatty Acid Complexes on Rat Hepatoma", Cells, *Cancer Res*, (1983), 43:2668-2672.

Dhopeshwarker, G., "Fatty Acid Transport Through the Blood-Brain Barrier.", *Biochim Biophys. Acta* 255:572-579, (1972).

Dischino, et al., "Synthesis of Monosodium Salt of Carbon-14 Labeled Paclitaxel (Taxol®) 2'-Ethyl Carbonate 7-Phophonooxymethyl Ether, a Potential Prodrug of Paclitaxel," *Journal of Labelled Compounds and Radiopharmaceuticals*, vol. XXXIX, No. 2.

D'Orlando, et al., "Citicoline (CDP-Choline): Mechanisms of Action and Effects in Ischemic Brain Injury", *Neurol. Res.* (1995) 17: 281-284.

Ehringer, W., et al., "A Comparison of the Effects of Linolenic (18:3 Omega 3) and Docosahexaenoic (22:6 Omega 3) Acids on Phospholipid Bilayers", *Chem Phys Lipids*, (1990), 54:79-88.

Ertel, et al., "Type III-Agatoxins: A Family of Probes for Similar Binding Sites on L- and N-Type Calcium Channels", *Biochemistry*, 33:5098-5108 (1994).

Falconer, J.S., et al., "Effect of Eicosapentaenoic Acid and Other Fatty Acids on the Growth in Vitro of Human Pancreatic Cancer Cell Lines", *Br. J. Cancer*, (1994,) 69:826-832.

Ferrari et al., "9-Cis-6,6'-Diapo-Gamma, Gamma-Carotenedioic Acid Derivatives and Pharmaceutical Compositions Containing Them", p. 710. Abs. 20423w, *Chem. Abs.* 95(23), Dec. 7, 1981,EP30,009 Jun. 10, 1981.

Garzon-Aburbeh, et al., "A Lymphotropic Product of L-Dopa:Synthesis" J. Med. Chem. 29: 687-691 (1986).

Georg et al., "The Medicinal Chemistry of Taxol", in "Taxol Science and Applications" ed. Matthew Suffness. Boca Raton: CRC Press, Inc., 1995, pp. 317-375.

Greenwald, et al., Highly Water Soluble Taxol Derivatives: 7-Polyethylene Glycol Carbamates and Carbonates, *J. Org. Chem.*, 1995, vol. 60, pp. 331-336.

Guénard, et al., "Efects of the Hydrophobicity of Taxoids on their Interaction with Tubulin", *Bioorganic & Medicinal Chemistry* vol. 8, (2000) pp. 145-156.

Guffy, M.M., et al., "Effect of Cellular Fatty Acid Alteration on Adriamycin Sensitivity in Cultured L1210 Murine Leukemia Cells", *Cancer Res*, (1984), 44:1863-1866.

Gunne, et al., "Oral Dyskinesia in Rats Following Brain Lesions and Neuroleptic Drug Administration", Psychopharmacology 77:134-139 (1982).

Halmos, et al. "Fatty Acid Conjugates of 2'-Deoxy-5'-Fluoroiridine as Prodrugs for the Selective Delivery of 5-Fluorouracil to Tumor Cells" *Biochemical Pharmacology*, (1992) 44:1:149-155.

Hesse et al., "Inhibitory Effect of Cholesteryl- -Aminobutyrate" Neurolpharmacology, vol. 24, No. 2, pp. 139-146 (1985).

Hesse, et al., "Uptake in brain neurophysiological activity of two lipid esters of gamma-aminobutyric acid" *Neuropharmacol.* 27:6:637-40 (1988).

Higuchi et al., (Editors), Prodrugs as Novel Drug Delivery Systems, Acs Symposium Series, vol. 14, ACS, Washington, 1975, pp. 14-15.

Hong et al., "Nucleoside-ether lipid conjugates as biotransformed prodrugs of antitumor and antiviral nucleosides" *Journal of Lipid Mediators and Cell Signalling*. 10: 159-161 (1994).

Iwakami, et al., "Inhibition of Arochidonate 5-Lipoxygenase by Phenolic Compounds", Chem. Pharm. Bull. (Japan), 34(9), 3960-3963 (1986).

Jacob, et al., "Synthesis, brain uptake and pharmacological properties of a glyceryl lipid containing GABA and the GABA-T inhibitor, gamma-vinyl-GABA," *J. Med. Chem.* 33:733-6 (1990).

Jacob, et al., "Alpha-Aminobutyric Acid Esters.2. Synthesis . . . ", Journal of Medicinal Chemistry, vol. 28, No. 1, pp. 106-110 (1985).

Jacob, et al., "Alpha-Aminobutyric Acid Esters.3. Synthesis, brain uptake and pharmacological properties of C-18 Glyceryl lipid esters of BAGA with varying degree of unsaturation," *J. Med. Chem.* 30:1573-6 (1987).

Jacobson, K., et al., Adenosine analogs with covalently attached lipids have enhanced potency at A1-adenosine receptors, *FEBS Letters* 225:1,2:97-102, (1987).

Jenski, L.J., et al., "Docosahexaenoic Acid-Induced Alteration of Thy-1 and Cd8 Expression on Murine Splenocytes", *Biochim Biophys Acta*, (1995), 1236(1):39-50.

Jenski, L.J., et al.,"Omega 3 Fatty Acids Increase Spontaneous Release of Cytosolic Components From Tumor Cells", *Lipids*, (1991), 26(5):353-358.

Jenski, L.J., et al., "Omega-3 Fatty Acid-Containing Liposomes in Cancer Therapy", *Proc Soc Exp Biol Med*, (1995), 210(3):227-233.

Karmali, R.A., et al., "Effect of Omega-3 Fatty Acids on Growth of a Rat Mammary Tumor", *J Natl Cancer Inst* (1984), 73(2):457-461. (Abstract).

Karmali, R., "N-3 Fatty Acids: Biochemical Actions in Cancer", *J. Nutr. Sci. Vitaminol.* (Tokyo), (1992), 148-152. (Abstract).

Kinsella, J.E., et al., "Effects of Polyunsaturated Fatty Acids on the Efficacy of Antineoplastic Agents Toward L5178y Lymphoma Cells", *Biochem Pharmacol*, (1993), 45(9):1881-1887. (Abstract).

Kretsinger, R. H., et al., "The EF-Hand, Homologs and Analogs", *Novel Calcium-Binding Proteins*, 17-37 (1991).

Konigstorfer et al., "Biosynthesis of Ependymins from Goldfish Brain", J. Biol. Chem., vol. 264 (23): 13689-13692 (1989).

(56) References Cited

OTHER PUBLICATIONS

Konigstorfer et al., "Molecular Characterization of an Ependymin Precursor from Goldfish Brain", J. Neurochem., 52:310-312 (1989).
Leonard, et al., "Identification and Characterization of mRNAs Regulated by Nerve Growth Factor in PC12 Cells", *Molecular and Cellular Biology*, 7(9):3156-67 (1987).
Lohr, et al., "Neuroleptic-Induced Movement Disorders . . . ", Psychiatry, vol. 3, 1-1 6 (1989).
Madhavi, N., et al., "Effect of N-6 and N-3 Fatty Acids on the Survival of Vincristine Sensitive and Resistant Human Cervical Carcinoma Cells In Vitro", *Cancer Lett*, (1994), 84:31-41.
Makino, et al., Chemical Abstracts, vol. 106, No. 12, (90177x) issued Mar. 23, 1987, "Pharmaceuticals Permeable to Blood-Brain Barrier".
Marder, S.R., *J. Clin. Psychiatry* (supp 3), *Management of Schizophrenia* 57:9-13 (1996).
Marsden, B. J., et al., "H NMR Studies of Synthetic Peptide Analogues of Calcium-Bining Site III of Rabbit Skeletal Troponin C: Effect of the Lanthanum Affinity of the Interchange of Aspartic Acid and Asparagine Residues at the Metal Ion Coordinating Positions", *Biochemistry*, 27:4198-4206 (1988).
Mazumdar, et al., "Preparation and Evaluation of Ethambutol Derivatives", Indian J. Pharm. Sci. 47(6): 179-180 (1985).
Meier et al., "Molecular Cloning of Bovine and Chick Nerve Growth (NGF) . . . ", *The EMBO Journal*, vol. 5, 7:1489-1493 (1986).
Minami, M., et al.,"Effects of Low-Dose Eicosapentaenoic Acid, Docosahexaenoic Acid and Dietary Fat on the Incidence, Growth and Cell Kinetics of Mammary Carcinomas in Rats", *Oncology*, (1996), 53(5):398-405.
Nicolaou et al., "Design, Synthesis and Biological Activity of Protaxols", *Nature*, 364: 464-466 (1993).
Nishio, et al., "Novel Water-soluble Derivatives of Docosahexaenoic Acid Increase Diacyl-Glycerol Production Mediated by Phosphatidylcholine-Specific Phospholipase C", *Proc. Soc. Exp. Biol. Med.* (1993) 203(2):200-208.
Oshima, M., et al., "Effects of Docosahexaenoic Acid (Dha) on Intestinal Polyp Development in Apc Delta 716 Apc Delta 716 Knockout Mice", *Carcinogenesis*, (1995), 16(11):2605-2607.
Pascale, A.W., et al., "Omega-3 fatty acid modification of membrane structure and function. Alteration by docosahexaenoic acid of tumor cell sensitivity to immune cytolysis", *Nutr Cancer*, (1993), 19(2):147-157.
Plumb, J.A., et al., "Effect of Polyunsaturated Fatty Acids on the Drug Sensitivity of Human Tumour Cell Lines Resistant to Either Cisplatin or Doxorubicin", *Br J Cancer*, (1993), 67:728-733.
Pouillart, "Role of Butyric Acid and its Derivatives in the Treatment of Colorectal Cancer and Hemoglobinopathies" *Life Sciences* (1998) 63:20:1739-1760.
Rocco et al., "Models of Fibronectin", The EMBO Journal, 6: 2343-2349 (1987).
Rose, W.C., Preclinical Antitumor Activity of Taxanes, in "Taxol Science and Applications" ed. Matthew Suffness. Boca Raton: CRC Press, Inc., 1995, pp. 209-235.
Schabitz, et al., "The effects of Prolonged Treatment with Citicoline in Temporary Experimental Focal Ischemia", *J. Neurol. Sci.*, (1996) 138(1-2):21-25 (Abstract).
Scott, et al., "Isolation and nucleotide sequence of cDNA encoding . . . ", Nature 3 02, 538-540 (1983).
Shashoua, et al., "Gamma-Aminobutyric Acid Esters.1. Synthesis . . . ", *J. of Med. C hem.*, vol. 27, pp. 659-664 (1984).
Shashoua, V.E., "Ependymin, a Brain Extracellular Glycoprotein, and CNS Plasticity," reprinted from *Activity-Driven CNS Changes in Learning and Development*, vol. 627 of the Annals of the New York Academy of Sciences, Aug. 5, 1991 ).
Shashoua, V.E., "The Role of Brain Extracellular Proteins . . . ", *Cellular an d Mol. Neurobiol.*, 5 (1/2):183-207 (1985).
Shashoua, et al., "Evidence for the In Vivo Polymerization of Ependymin: Brain Extracellular Glycoprotein", Brain Research, 522, 181-190 (1990).
Shashoua, V.E., "The role of ependymin in the development of long lasting synaptic charges" *J. Physiol.* Paris, 83:232-239 (1988-1989).
Shea, et al., "Effect of Retinoic Acid on Growth and Morphological Differentiation of Mouse NB2a Neuroblastoma Cells in Culture", *Developmental Brain Research*, 21:307-314 (1985).
Spector, R., "Fatty Acid Transport Through the Blood-Brain Barrier.", *J. of Neurochem.*, 50:2:639-643 (1988).
Suphioglu, C., et al., "Molecular Cloning and Immunological Characterization of Cyn d 7, A Novel Calcium-Binding Allergin from Bermuda Grass Pollen", *FEBS Letters*, 402:167-172 (1997).
Swindell, et al., "Characterization of the Taxol Structure-Activity Profile for the Locus of the A-Ring Side Chain Side Chain", *Bioorganic & Medicinal Chem. Ltrs.*, vol. 4, No. 12, pp. 1531-1536. (1994).
Terasawa, et al., "Neurocalcin a novel calcium binding protein from bovine brain" *J. Biol. Chem.*, 267:27 (1992), pp. 19596-19599.
Tessier, C., et al., "Docosahexaenoic Acid is a Potent Inhibitor of Rat Uterine Stromal Cell Proliferation", *Biochem Biophys Res Commun*, (1995), 207(3):1015-1021.
Tinsley, I.J., et al., "Influence of Dietary Fatty Acids on the Incidence of Mammary Tumors in the C3h Mouse", Ch3h Mouse, *Cancer Res*, (1981), 41:1460-1465.
Ueda, et al., "Synthesis and Antitumor Evaluation of 2'-Oxycarbonylpaclitaxels (Paclitaxel-2'-Carbonates)," *Bioorganic & Medicinal Chemistry Letters*, vol. 4, No. 15, pp. 1861-1864, 1994.
Yamamoto et al., "The Survival of Rat Cerebral Cortical Neurons in the Presence of Trophic APP Peptides" *J. Neurobiol.* 25, 585-594 (1994).
Yokokawa, et al., "The Synthesis of Rat Cerebral Cortical Neurons in the Presence of EF-Hand Type Calcium-Binding Peptides" *Chem. Lett*, 1627-1630 (1989).
Young, et al., "Differentiation of PC12 cells in response to a cAMP analogue is accompanied by sustained activation of mitogen-activated protein kinase Comparison with the effects of insulin, growth factors and phorbol esters", *FEBS Letters*, 338:212-216 (1994).
Zerouga, M., et al., "Phospholipid Class as a Determinant in Docosahexaenoic Acid's Effect on Tumor Cell Viability", *Anticancer Res*, (1996), 16:2863-2868. (Abstract).
Zijlstra, J.G., et al., "Influence of Docosahexaenoic Acid In Vitro on Intracellular Adriamycin Concentration in Lymphocytes and Human Adriamycin-Sensitive and Resistant Small-Cell Lung Cancer Cell Lines, and on Cytotoxicity in the Tumor Cell Lines", *Int J Cancer*, (1987), 40:850-856.
Aihara, M., et al., "Effects of liposteroid on skin lesions in autoimmune MRL*lpr/lpr* mice," *J. of Dermatological Science* 16 (1997), pp. 45-51.
Bolwell, et al., "High dose cytarabine: a review," *Leukemia* 5 (May 1988), pp. 253-260.
"Cytosar-U cytarabine for injection, USP," Product insert, Feb. 2002.
DeVita, Jr., et al., *Cancer Principles & Practice of Oncology*, 5th Ed., pp. 443-444, (1997).
"Dexamethasone palmitate: Chemical Teratogens, Carcinogens, Mutagens," CAS# [33755-46-3], ACX# [11012259], http://www.evol.nw.ru/labs/lab38/spirov/hazard/dexamethasone_palmitate.html.
Funauchi, M., et al., "Effects of liposteroid on the hemophagocytic syndrome in systemic lupus erythematosus," *Lupus* 12 (2003), pp. 483-485.
Haas, et al., "Effektivität intramuskulär verabreichten Cytosin-Arabinosids bei der ambulanten Behandlung von Kindem mit akuter Leukämie in Remission," *Onkology* (Feb. 1980) pp. 53-57. (English summary included).
Ho, et al., "Pharmacology of 5'-Esters of 1-β-D-Arabinofuranosylcytosine," *Cancer Research* 37 (Jun. 1977), pp. 1640-1643.
Ho, et al., "Pharmacologic Studies of Cyclocytidine and Arabinosylcytosine in Dogs," *Drug Metabolism and Disposition* 3(4) (1975), pp. 309-313.
Hoshi, K., et al., "Double-blind study with liposteroid in rheumatoid arthritis," *Drugs Exptl. Clin. Res.* XI(9) (1985), pp. 621-626.
Kataoka, et al., "Effect and Mode of Action of $N^4$-Behenoyl-β-D-Arabinofuranosylcytosine," *Recent Results in Cancer Research* 70 (1980), pp. 147-151.

(56) References Cited

OTHER PUBLICATIONS

Mizushima, Y., et al., "Tissue distribution and anti-inflammatory activity of corticosteroids incorporated in lipid emulsion," *Annals of the Rheumatic Diseases*, 41 (1982), pp. 263-267.

Rentsch, et al., "Pharmacokinetics of $N^4$-Octadecyl-1-β-D-Arabinofuranosylcytosine in Plasma and Whole Blood after Intravenous and Oral Administration to Mice," *J. Pharm. Pharmacol.* 49 (1997), pp. 1076-1081.

Seki, J., et al., "A nanometer lipid emulsion, lipid nano-sphere (LNS®), as a parenteral drug carrier for passive drug targeting," *International Journal of Pharmaceutics* 273 (2004), pp. 75-83.

Yokoyama, K., et al., "Development of a corticosteroid incorporated in lipid microspheres (liposteroid)," *Drugs Exptl. Clin. Res.* XI(9) (1985), pp. 611-620.

Yoshida, et al., *Cancer and Chemotherapy* 14(6) (1987), Part I, pp. 1820-1824—English Abstract.

Yoshida, et al., "Pharmacokinetics of High Dose Treatments of $N^4$-Behenoyl-1-β-D-Arabinofuranosylcytosine (BH-AC)" *Cancer and Chemical Treatment (Cancer and Chemotherapy)* 14(6) (1987), Part I, pp. 1820-1824—English Translation.

Yoshida, et al., "$N^4$-Behenoyl-1-β-D-Arabinofuranosylcytosine(BH-AC) Pharmacokinetics" *Cancer and Chemical Treatment (Cancer and Chemotherapy)* 14(6) (1987), Part I, pp. 1820-1824—Japanese Language (English Summary included at the end).

Supplementary partial European search report from related European Patent Application EP 02731170.3, dated Jun. 22, 2005.

Attard, George S., et al., "Phase behaviour of novel phospholipid analogues." Chemistry and Physics of Lipids, vol. 76, 1995, pp. 41-48.

Database Beilstein: Jun. 29, 1989, XP002329550; Database accession No. 2199386 (BRN), Abstract & SU 477 159 A (Strel'Tsov, Bliznyuk) 1976.

Database HCAPLUS ACS: May 12, 1984; XP002329551; Retrieved from STN Database accession No. 93:90207/DN; Abstract, RN52067-53-5, 74551-09-0 & JP 55 053208 A (Mitsubishi Chemical Ind. Co.); Apr. 18, 1980.

Database HCAPLUS ACS; Jun. 28, 1991; XP002329552; Retrieved from STN Database accession No. 114:254032, Abstract, RN29271-27-0, 49802-20-2, 134036-50-3 & JP 02 256624 A (Sagami Chemical Research Center) Oct. 17, 1990.

Database HCAPLUS ACS: Jul. 2, 1998; XP002329553; Retrieved from STN Database accession No. 129:135899/DN, Abstract, RN210540-30-0, -31-1 & JP 10 168047 A (KAO Corp.), Jun. 23, 1998.

Database HCAPLUS ACS: Oct. 11, 2000; XP002329554; Retrieve from STN Database accession No. 134:193273/DN, Abstract, RN327082-01-9; & Chen, Zai-Xin et al: Zhongguo Yiyao Gongye Zazhi Bianjibu, vol. 31, No. 6, 2000, pp. 265-268.

Domagala, John M., et al., "New Class of Anti-HIV-1 Agents Targeted Toward the Nucleocapsid Protein NCp7: The 2,2'-Dithiobisbenzamides." Bioorganic & Medicinal Chemistry, vol. 5, No. 3, pp. 569-579 (1997).

Janusz, John J., et al., "Vanilloids. I. Analogs of Capsaicin with Antinociceptive and Antiinflammatory Activity." J. Med. Chem., vol. 36, No. 18, pp. 2595-2604 (1992).

Kageyama, Yuichi, et al., "Novel approaches to prodrugs of anticancer diaminodichloroplatinum(II) complexes activated by stereoselective enzymatic ester hydrolysis." Journal of Inorganic Biochemistry, vol. 70, pp. 25-32 (1998).

Kalgutkar, Amit S., et al., "Ester and Amide Derivatives of the Nonsteroidal Antiinflammatory Drug, Indomethacin, as Selective Cyclooxygenase-2 Inhibitors." Journal of Medicinal Chemistry, pp. 2860-2870 (2000).

Kariko, Katalin, et al, "n-DECYL-NHpppA2' p5' A2' p5' A A Phosphatase-Resistant, Active pppA2'p5' A2' p5' A Analog." Biochemical and Biophysical Research Communications, vol. 128, No. 2, pp. 695-698 (1985).

McGuigan, C., et al., "Synthesis and Evaluation of some masked phosphate esters of the anti-herpesvirus drug 882C (netivudine) as potential antiviral agents." Antiviral Chemistry & Chemotherapy, vol. 9, pp. 233-243 (1998).

McGuigan, C. et al., "Phosphoramidates as potent prodrugs of anti-HIV nucleotides: studies in the amino region." Antiviral Chemistry & Chemotherapy, vol. 7, No. 1, pp. 31-36 (1996).

Miroshnikova, Olga V., et al., "Structure-Activity Relationship in the Series of Eremomycin Carboxamides." The Journal of Antibiotics, vol. 53, No. 3, pp. 286-293 (2000).

Nicotaou, Anna, et al., "Synthesis and Properties of Novel Lipopeptides and Lipid Mimetics." Journal of Peptide Science, vol. 3, pp. 291-298 0997).

Rasmusson, Gary H., "Azasteroids: Structure-Activity Relationships for Inhibition of 5α-Reductase and Androgen Receptor Binding." J. Med. Chem., vol. 29, pp. 2298-2315 (1986).

Smrt$^a$, J., et al., "Synthesis of Some Nucleolipids." Collection Czechoslov. Chem. Commun., vol. 45, pp. 927-931 (1980).

Turesky, Samuel, et al., "In Vitro Chemical Inhibition of Plaque Formation." J. Periodontol., vol. 43, pp. 263-269 (1972).

* cited by examiner

FATTY AMINE DRUG CONJUGATES

RELATED APPLICATION

This application claims priority under 35 U.S.C. §119 (e) from U.S. provisional patent application Ser. No. 60/278,552, filed on Mar. 23, 2001, entitled Fatty Amine Drug Conjugates. The contents of the provisional application are expressly incorporated herein by reference.

FIELD OF THE INVENTION

The invention relates to conjugates of fatty amines and pharmaceutical agents such as anticancer, antiviral, and antipsychotic agents useful, for example, in treating cancer, viruses, and psychiatric disorders, and compositions and formulations thereof. Methods for making and using the conjugates also are provided.

BACKGROUND OF THE INVENTION

Improving drug selectivity for target tissue is an established goal in the medical arts. In general, it is desirable to deliver a drug selectively to its target, so that dosage and, consequently, side effects can be reduced. This is particularly the case for toxic agents such as anticancer agents because achieving therapeutic doses effective for treating the cancer is often limited by the toxic side effects of the anticancer agent on normal, healthy tissue.

Extensive research has been done on the use of fatty acids as agents that improve selectivity of drugs for their target tissues. Fatty acids previously have been conjugated with drugs to help the drugs as conjugates cross the blood brain barrier. DHA (docosahexaenoic acid) is a 22 carbon naturally-occurring, unbranched fatty acid that previously has been shown to be unusually effective, when conjugated to a drug, in crossing the blood brain barrier. DHA is attached via the acid group to hydrophilic drugs and renders these drugs more hydrophobic (lipophilic). The mechanism of action by which DHA helps drugs conjugated to it cross the blood brain barrier is unknown.

Another example of the conjugation of fatty acids to a drug is the attachment of pipotiazine to stearic acid, palmitic acid, enanthic acid, undecylenic acid or 2,2-dimethyl-palmitic acid. Pipotiazine is a drug that acts within the central nervous system. The purpose of conjugating pipotiazine to the fatty acids was to create an oily solution of the drug as a liquid implant for slow release of the drug when injected intramuscularly. The release of the drug appeared to depend on the particular fatty acid selected, and the drug was tested for its activity in the central nervous system.

Lipidic molecules, including fatty acids, also have been conjugated with drugs to render the conjugates more lipophilic than the unconjugated drugs. In general, increased lipophilicity has been suggested as a mechanism for enhancing intestinal uptake of drugs into the lymphatic system, thereby enhancing the entry of the conjugate into the brain and also thereby avoiding first-pass metabolism of the conjugate in the liver. The type of lipidic molecules employed have included phospholipids, non-naturally occurring branched and unbranched fatty acids, and naturally occurring branched and unbranched fatty acids ranging from as few as 4 carbon atoms to more than 30 carbon atoms. In one instance, enhanced receptor binding activity was observed (for an adenosine receptor agonist), and it was postulated that the pendant lipid molecule interacted with the phospholipid membrane to act as a distal anchor for the receptor ligand in the membrane micro environment of the receptor. This increase in potency, however, was not observed when the same lipid derivatives of adenosine receptor antagonists were used, and generalizations thus were not made possible by those studies.

Of key importance in the treatment of cancer, viruses, and psychiatric illness is the selectivity and targeting of drugs to tissues. The increased targeting reduces the amount of pharmaceutical agents needed, and the frequency of administration of the pharmaceutical agents, both features especially important in treatments that involve administration of pharmaceutical agents that may be toxic to surrounding tissues and may cause side effects. Because of the critical importance of effective treatments for cancer, viral diseases and psychiatric disorders and the difficulty in selectively targeting the affected tissues, there is presently a need for effective methods to target tissues with powerful drugs, while also reducing the side effects and difficult administration regimens.

Fatty amines are lipidic molecules terminating in an amino group (unlike fatty acids, which, of course, terminate in a carboxylic acid group). Unlike fatty acids, fatty amines are not a prevalent tissue component of mammals. They typically are prepared synthetically using fatty acids as a starting material.

SUMMARY OF THE INVENTION

The invention relates to the surprising discovery that fatty amines can be conjugated to pharmaceutical agents for treatment of a variety of disorders, including but not limited to cancer, viral infections, and psychiatric diseases. The benefits of these pharmaceutical-fatty amine conjugates include one or more of the following: targeting of the drug to the tissue of interest; favorably affecting the volume of distribution of the drug in the tissue of interest; reducing toxicity of the drug; reducing side effects of the drug; reducing clearance of the drug; reducing the necessary volume and/or frequency of administration of the drug, or
increasing the amount of drug that a subject can tolerate by favorably affecting volume of distribution, tissue distribution, and/or release kinetics of active drug from an inactive conjugate in certain embodiments. Another surprising aspect of the fatty amine-pharmaceutical agent conjugates is that once the fatty amines are separated from conjugation to the pharmaceutical agents in vivo, the fatty amines may be metabolized and eliminated.

Any and all of these aforementioned characteristics of the fatty amine-pharmaceutical agent conjugates may benefit subjects in need of treatment for diseases such as cancer, psychiatric disorders, and viral diseases and may allow altered dosages of drugs to be administered less frequently, with better results and fewer side effects.

According to one aspect of the invention, compositions of matter are provided. The compositions, or compounds, comprise pharmaceutical agents (i.e., drugs) conjugated to fatty groups of fatty amines via a carbamate linkage and have the following formula:

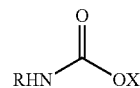

wherein R is a $C_8$-$C_{26}$ fatty group of a fatty amine $RNH_2$ and X is a pharmaceutical agent moiety of a pharmaceutical agent XOH.

According to another aspect of the invention, pharmaceutical agents conjugated to fatty amines via phosphoramide linkages are provided. The compounds have the formula:

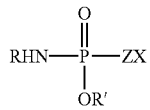

wherein R is a $C_8$-$C_{26}$ fatty group of a fatty amine $RNH_2$, X is a pharmaceutical agent moiety of a pharmaceutical agent XZH, wherein Z is O, a primary amino group, or a secondary amino group, and R' is H, an ion, or a protecting group.

According to another aspect of the invention, pharmaceutical agents conjugated to fatty amines via phosphonamide linkages are provided. The compounds have the formula:

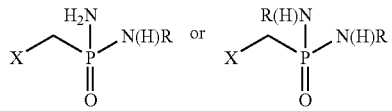

wherein R is a $C_8$-$C_{26}$ fatty group of a fatty amine $RNH_2$, X is a pharmaceutical agent moiety of a pharmaceutical agent $XCH_2PO_3H_2$, $XCHR'PO_3H_2$, or $XCR'R''PO_3H_2$, wherein R' and R" are independently selected from alkyl, alkenyl, aryl, alkyl-substituted heteroatom, alkenyl-substituted heteroatom, an aryl-substituted heteroatom, and the like.

According to another aspect of the invention, pharmaceutical agents conjugated to fatty amines via urea (or carbamate) linkages are provided. These compounds have the formula:

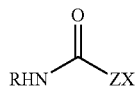

wherein R is a $C_8$-$C_{26}$ fatty group of a fatty amine $RNH_2$, X is a pharmaceutical agent moiety of a pharmaceutical agent XZH, wherein Z is O, a primary amino group, or a secondary amino group.

According to another aspect of the invention, pharmaceutical agents conjugated to fatty amines via amide linkages are provided. These compounds have the following formula:

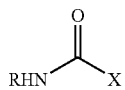

wherein R is a $C_8$-$C_{26}$ fatty group of a fatty amine $RNH_2$ and X is a pharmaceutical agent moiety of a pharmaceutical agent XC(O)OH.

According to yet another aspect of the invention, pharmaceutical agents conjugated to fatty amines via thionocarbamate linkages are provided. These compounds are of the formula:

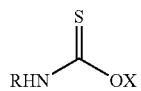

wherein R is a $C_8$-$C_{26}$ fatty group of a fatty amine $RNH_2$ and X is a pharmaceutical agent moiety of a pharmaceutical agent XOH.

According to still another aspect of the invention, pharmaceutical agents linked to fatty amines via thiourea linkages are provided. These compounds are of the formula:

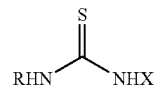

wherein R is a $C_8$-$C_{26}$ fatty group of a fatty amine $RNH_2$ and X is a pharmaceutical agent moiety of a pharmaceutical agent $XNH_2$.

According to yet another aspect of the invention, pharmaceutical agents conjugated to fatty amines via guanidine linkages are provided. These compounds are of the formula:

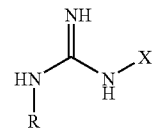

wherein R is a $C_8$-$C_{26}$ fatty group of a fatty amine $RNH_2$ and X is a pharmaceutical agent moiety of a pharmaceutical agent $XNH_2$ (or XOH).

In certain embodiments, the fatty amine moiety has a carbon structure that is the same as the carbon structure of a naturally occurring fatty alcohol or acid. In some embodiments, the fatty amine moiety has a carbon structure which is the same as the carbon structure of fatty acids which occur naturally in humans. Preferably, the fatty amine moiety has a carbon structure which is the same as a $C_{12}$-$C_{26}$, and even more preferably a $C_{14}$-$C_{24}$, fatty acid occurring naturally in humans.

In other embodiments, the fatty amine moiety has a carbon structure that is the same as an unnatural fatty alcohol or acid. In some embodiments, the fatty amine moiety has an even number of carbon atoms. In other embodiments, the fatty amine moiety has an odd number of carbon atoms. In some embodiments, the carbon structure is saturated and in other embodiments, the carbon structure is unsaturated (olefinic). Preferably, the carbon structure is unsaturated, that is, has at least one double bond.

In some embodiments, the fatty amine moiety has a carbon structure that is the same as any of the following fatty acids: caprylic acid, capric acid, undecylenic acid, lauric acid, myristic acid, palmitic acid, palmitoleic acid, stearic acid, oleic acid, vaccenic acid, linoleic acid, linolenic acid, eleostearic acid, gondoic acid, arachidonic acid, eicosapentaenoic acid, docosenoic acid, docosatetraenoic acid, docosapentaenoic acid, docosahexaenoic acid, and nervonic acid. These fatty acids encompass all of the various possible isomers, including (E) and (Z) stereochemistry about the double bonds as well as placement of the double bonds. For example, as used herein, linolenic acid encompasses γ-linolenic acid, dihomo-γ-linolenic acid, as well as α-linolenic acid which differ by the placement of the double bonds in the carbon chain but have the same molecular formula (and molecular weight).

In some embodiments, the fatty amine moiety has a carbon structure the same as a fatty acid selected from the group consisting of: octanoic (caprylic); nonanoic (pelargonic); decanoic (capric); undecanoic (hendecanoic); dodecanoic (lauric); tridecanoic; tetradecanoic (myristic); pentadecanoic; hexadecanoic (pamitic); heptadecanoic (margaric); octadecanoic (stearic); 12-hydroxy stearic; nonadecanoic; eicosanoic (arachidic); heneicosanoic; docosanoic (behenic); tricosanoic; and tetracosanoic (lignoceric).

In these and other embodiments, the fatty amine moiety has a carbon structure the same as a fatty acid selected from the group consisting of: 10-undecenoic (hendecenoic); 11-dodecenoic; 12-tridecenoic; 9-tetradecenoic (myristoleic); 9-trans-tetradecenoic (myristelaidic); 10-pentadecenoic; 10-trans-pentadecenoic; 9-hexadecenoic (palmitoleic); 8-trans-hexadecenoic (palmitelaidic); 10-heptadecenoic; 10-trans-heptadecenoic; 6-octadecenoic (petroselinic); 6-trans-octadecenoic (petroselaidic); 8-octadecenoic (oleic); 9-11-octadecenoic (vaccenic); 11-trans-octadecenoic (transvaccenic); 9-cis-12 hydroxy-octadecenoic (ricinoleic); 9-trans-12-hydroxy-octadecenois (ricinelaidic); 7-nonadecenoic; 7-trans-nonadecenoic; 10-nonadecenoic; 10-trans-nonadecenoic; 10-13-nonadecadienoic; 10-13-trans-nonadecadienoic; 8-12-octadecadienoic (linoleic); 9-trans-12-trans octadecadienoic (linoelaidic); octadecadienoic (conjugated); 9-12-15-octadecatrienoic (linolenic); 6-9-12-octadecatrienoic (gamma linolenic); 11-trans-eicosenoic; 8-eicosenoic; 11-eicosenoic; 5-eicosenoic; 11-14-eicosadienoic; 8-11-14-eicosatrienoic (homogamma linolenic); 11-14-17-eicosatrienoic; 5-8-11-14-eicosatetraenoic (arachidonic); 5-8-11-14-17-eicosapentaenoic; 7-10-13-16-19-docosapentaenoic; arachidonic; 13-docosenoic (erucic); 13-transdocosenoic (brassidic); 13-16-docosadienoic; 13-16-19-docosatrienoic; 7-10-13-16-docosatetraenoic; 4-7-10-13-16-19-docosahexaenoic (DHA); 12-heneicosenoic; 12-15-heneicosadienoic; 14-tricosenoic; and 15-tetracosenoic (nervonic).

Many pharmaceutical agents are useful in the present invention. As those skilled in the art will recognize, any pharmaceutical agent having a group to which a fatty amine may be conjugated (either directly or via a linkage as described) is useful in the present invention. Such pharmaceutical agents contain groups such as —OH, —NH$_2$, —NHR', —CO$_2$H, —SH, —PO$_3$H$_2$, and the like (wherein R' denotes a group such as alkyl, aryl, alkenyl, alkynyl, etc.). Many pharmaceutical agents, such as flavopiridol, contain more than one group to which fatty amines may be conjugated. As those skilled in the art will recognize, it is possible to choose which group of the pharmaceutical agent the fatty amine will be conjugated to by using, for example, well know protection and deprotection strategies. Generally, conjugation of just one fatty amine moiety to one pharmaceutical agent is preferable, although one skilled in the art will recognize that conjugation of more than one fatty amine to one pharmaceutical agent is possible.

In certain embodiments, the pharmaceutical agent may be selected from an adrenergic agent; adrenocortical steroid; adrenocortical suppressant; amine deterrent; aldosterone antagonist; amino acid; ammonia detoxicant; anabolic; analeptic; analgesic; androgen; anesthesia; anesthetic; anorectic; antagonist; anterior pituitary suppressant; anthelmintic; antiacne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; anti-emetic; anti-epileptic; anti-estrogen; antifibrinolytic; antifingal; anti-glaucoma agent; antihemophilic; antihemorrhagic; antihistamine; antihyperlipidemic; antihyperlipoproteinemic; antihypertensive; antihypotensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory, antispasmodic; antithrombotic; antitussive; anti-ulcerative; antiurolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; impotence therapy adjunct; inhibitor; keratolytic; LNRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine A1 antagonist; serotonin antagonist; serotonin inhibitor; serotonin receptor antagonist; steroid; stimulant; suppressant; symptomatic multiple sclerosis; synergist; thyroid hormone; thyroid inhibitor; thyromimetic; tranquilizer; agent for treatment of amyotrophic lateral sclerosis; agent for treatment of cerebral ischemia; agent for treatment of Paget's disease; agent for treatment of unstable angina; uricosuric; vasoconstrictor; vasodilator; vulnerary; wound healing agent; and xanthine oxidase inhibitor.

In certain important embodiments, the pharmaceutical agent is an anticancer agent. Important anticancer agents include: Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormiaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; FK-317; FK-973; FR-66979; FR-900482; Gemcitabine; Gemcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabinofluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl) -N'-cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis(platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine and (2-F-ara-AMP); 2-chlorodeoxyadenosine (2-Cda).

Other anti-neoplastic compounds include 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin $A_2$; bleomycin $B_2$; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; episteride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl amine; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bisacridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoictin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Other anticancer agents include antiproliferative agents (e.g., piritrexim isothionate), antiprostatic hypertrophy agent (e.g., sitogluside), benign prostatic hyperplasia therapy agents (e.g., tamsulosin hydrochloride), prostate growth inhibitor agents (e.g., pentomone), and radioactive agents: fibrinogen I 125; fludeoxyglucose F 18; fluorodopa F 18; insulin I 125; insulin I 131; iobenguane I 123; iodipamide sodium I 131; iodoantipyrine I 131; iodocholesterol I 131; iodohippurate sodium I 123; iodohippurate sodium I 125; iodohippurate sodium I 131; iodopyracet I 125; iodopyracet I 131; iofetamine hydrochloride I 123; iomethin I 125; iomethin I 131; iothalamate sodium I 125; iothalamate sodium I 131; iotyrosine I 131; liothyronine I 125; liothyronine I 131; merisoprol acetate Hg 197; merisoprol acetate Hg 203; merisoprol Hg 197; selenomethionine Se 75; technetium Tc 99m antimony trisulfide colloid; technetium Tc 99m bicisate; technetium Tc 99m disofenin; technetium Tc 99m etidronate; technetium Tc 99m exametazime; technetium Tc 99m furifosmin; technetium Tc 99m gluceptate; technetium Tc 99m lidofenin; technetium Tc 99m mebrofenin; technetium Tc 99m medronate; technetium Tc 99m medronate disodium; technetium Tc 99m mertiatide; technetium Tc 99m oxidronate; technetium Tc 99m pentetate; technetium Tc 99m pentetate calcium trisodium; technetium Tc 99m sestamibi; technetium Tc 99m siboroxime; technetium Tc 99m succimer; technetium Tc 99m sulfur colloid; technetium Tc 99m teboroxime; technetium Tc 99m tetrofosmin; technetium Tc 99m tiatide; thyroxine I 125; thyroxine I 131; tolpovidone I 131; triolein I 125; and triolein I 131.

Another category of anticancer agents useful as pharmaceutical agents in the present invention include anticancer supplementary potentiating agents. Anticancer supplementary potentiating agents include tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); calmodulin inhibitors (e.g., prenylamine, trifluoroperazine and clomipramine); amphotericin B; triparanol analogues (e.g., tamoxifen); antiarrhythmic drugs (e.g., quinidine); antihypertensive drugs (e.g., reserpine); thiol depleters (e.g., buthionine and sulfoximine) and multiple drug resistance reducing agents such as Cremaphor EL.

One particularly preferred class of anticancer agents for use in the present invention are taxanes. Among the taxanes, paclitaxel and docetaxel are preferred. Another preferred anticancer agent for use in the present invention is flavopirodol. Other important anticancer agents are annonaceous acetogenins and SN-38.

Another category of pharmaceutical agents for use in the present invention is antipsychotic agents. Antipsychotic agents include lorazepam; chlordiazepoxide; clorazepate; diazepam; alprazolam; hydroxyzine; buspirone; venlafaxine; mephobarbital; meprobamate; doxepin; perphenazine;

hydroxyzine pamoate; venlafaxine; mirtazapine; nefazodone; bupropion; phenelzine; tranylcypromine; citalopram; paraxefine; sertraline; amitrptyline; protriptyline; divalproex; clonazepam; clozapine; haloperidol; loxapine; molindone; thiothixene; pimozide; risperidone; quefiapine; thiothixen; olanzapine; quetiapine; prochlorperazine; mesoridazin; trifluoperazine; chlorpromazine; perphenazine; and fluvoxamine.

Another category of pharmaceutical agents useful in the present invention is antiviral agents. Antiviral agents include nucleoside analogs, nonnucleoside reverse transcriptase inhibitors, protease inhibitors, integrase inhibitors, including the following: Acemannan; Acyclovir; Acyclovir Sodium; Adefovir; Alovudine; Alvircept Sudotox; Amantadine Hydrochloride; Aranotin; Arildone; Atevirdine Mesylate; Avridine; BRL 47923; BRL 44385; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Indinavir; Kethoxal; Lamivudine; Lobucavir; Memotine Hydrochloride; Methisazone; Nelfinavir; Nevirapine; Penciclovir; Pirodavir; Ribavirin; Rimantadine Hydrochloride; Ritonavir; Saquinavir Mesylate; Somantadine Hydrochloride; 7-hydroxystaurosporine, Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime, and integrase inhibitors. Adefovir, cidofovir, BRL 47923, and BRL 44385 are particularly important pharmaceutical agents.

Particularly preferred pharmaceutical agents useful in the present invention include: annonaceous acetogenins; asimicin; rolliniastatin; guanacone, squamocin, bullatacin; squamotacin; taxanes; methotrexate FR-900482; FK-973; 3, FR-66979; FK-317; 5-FU; FUDR; FdUMP; Hydroxyurca; meta-pac; irinotecan; SN-38; 10-OH campto; topotecan; adriamycin; cis-Pt; carbo-Pt; bleomycin; mitomycin C; mithramycin; capecitabine; cytarabine; 2-Cl-2'deoxyadenosine; fludarabine-$PO_4$; mitoxantrone; mitozolomide; pentostatin; tomudex, TMC-125, TMC-114, valganciclovir; fomivirsen; zanamivir; oseltamivir; rimantadine; adefovir dipivoxil; tenofovir; tenofovir disoproxil;viramidine; 3-deazaneplanocin A; neplanocin A; saquanivir; maribavir; N-methanocarbathymidine; fusaric acid; synguanol; glycyrrhyzic acid; fludarabine; entecavir; and MIV-210.

Other particularly preferred pharmaceutical agents for use in the present invention include: gemcitabine, docetaxel, paclitaxel, vincristine, vinblastine, vinorelbine, SN-38, BRL 47923, BRL 44385, cidofivor, anhydrovinblastine, flavopiridol, purvalanol A, purvalanol B, aminopurvalanol, roscovitine, etoposide, 7-ethyl-10-hydroxycamptothecin, 10-hydroxycamptothecin, doxorubicin, mitomycin C, mithracin, epothilone B, epothilone D, camptothecin, discodermolide, and adefovir (PMEA).

One skilled in the art will readily recognize those pharmaceutical agents are suitable for conjugation with fatty amines with no more than routine skill. For example, one skilled in the art will recognize that flavopiridol does not contain a carboxylic acid moiety and as a result, it is inconvenient to synthesize a conjugate with an amide linkage. Preferred pharmaceutical agents are shown in Table 1, along with preferred linkages.

TABLE 1

FATTY AMINE PHARMACEUTICAL AGENT CONJUGATES

|  | Carbamate | Phosphoramide | Urea | Thiourea |
|---|---|---|---|---|
| Paclitaxel | X | X |  |  |
| Docetaxel | X | X |  |  |
| Gemcitabine | X | X | X | X |
| Vincristine | X | X | X | X |
| Vinblastine | X | X | X | X |
| Camptothecin | X | X |  |  |
| CPT-11 | X | X |  |  |
| SN-38 | X | X |  |  |
| Mitomycin C |  | X | X | X |
| Doxorubicin | X | X | X | X |
| Adefovir |  | X | X | X |
| BRL 47923 |  | X | X | X |
| BRL 44385 | X | X | X | X |
| Roscovotine | X | X | X | X |
| Purvalanol A | X | X | X | X |
| Puvalanol B | X | X | X | X |
| Flavopiridol | X | X |  |  |
| Cidofovir | X | X | X | X |
| Ribavirin | X | X |  |  |

|  | Amide | Thionocarbamate | Phosphonamide |
|---|---|---|---|
| Paclitaxel |  | X |  |
| Docetaxel |  | X |  |
| Gemcitabine |  | X |  |
| Vincristine | X | X |  |
| Vinblastine | X | X |  |
| Camptothecin |  | X |  |
| CPT-11 |  | X |  |
| SN-38 |  | X |  |
| Mitomycin C |  |  |  |
| Doxorubicin |  | X |  |
| Adefovir |  |  | X |
| BRL 47923 |  |  | X |
| BRL 44385 |  | X |  |
| Roscovotine |  | X |  |
| Purvalanol A |  | X |  |
| Puvalanol B | X | X |  |
| Flavopiridol |  | X |  |
| Cidofovir |  | X | X |
| Ribavirin |  | X |  |

Although the above examples are preferred, they are not limiting. Other conjugates may be synthesized according to the invention.

According to another aspect of the invention, compositions of matter are provided. The compositions are useful as intermediates to fatty amine pharmaceutical agent conjugates and are isocyanates of the following formula:

R—N=C=O wherein R is a $C_8$-$C_{26}$ fatty group of a fatty amine $RNH_2$.

According to another aspect of the invention, compounds useful as intermediates to the pharmaceutical agent fatty amine conjugates of the formula:

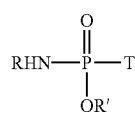

are provided wherein R is a $C_8$-$C_{26}$ group of a fatty amine $RNH_2$, R' is H, an ion, or a protecting group and T is a leaving group.

According to yet another aspect of the invention, compounds which are useful as intermediates in the synthesis of pharmaceutical agent fatty amine conjugates are provided. These compounds are of the formula:

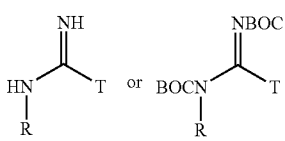

wherein R is a $C_8$-$C_{26}$ group of a fatty amine $RNH_2$, T is a leaving group, and BOC is a tert-butoxy group.

In certain embodiments, the leaving group T is OH, a halogen, or another leaving group. Particularly important leaving groups include N-hydroxysuccinimidyl, N-hydroxphthalimidyl, imidazoyl, para-nitrophenyl, ortho-nitrophenyl, azido, hydroxybenzotriazolyl, chloro, fluoro, N-hydroxymaleimidyl, pentafluorophenyl, 2,4,5-trichlorophenyl, 2,4,6-trichlorophenyl, 1-hydroxypiperidinyl, pentacholorphenyl, 3,4,5-trimethoxyphenyl, hydroxypyridinyl, 4-dimethylaminopyridinyl, 1-triazolopyridinyl, pyrazolyl, 3,5-dimethylpyrazolyl, and 1H-1,2,3-triazaolo-[4,5-b]pyridinyl. These leaving groups may optionally be substituted with electron withdrawing groups or electron donating groups. Other leaving groups include, but are not limited to:

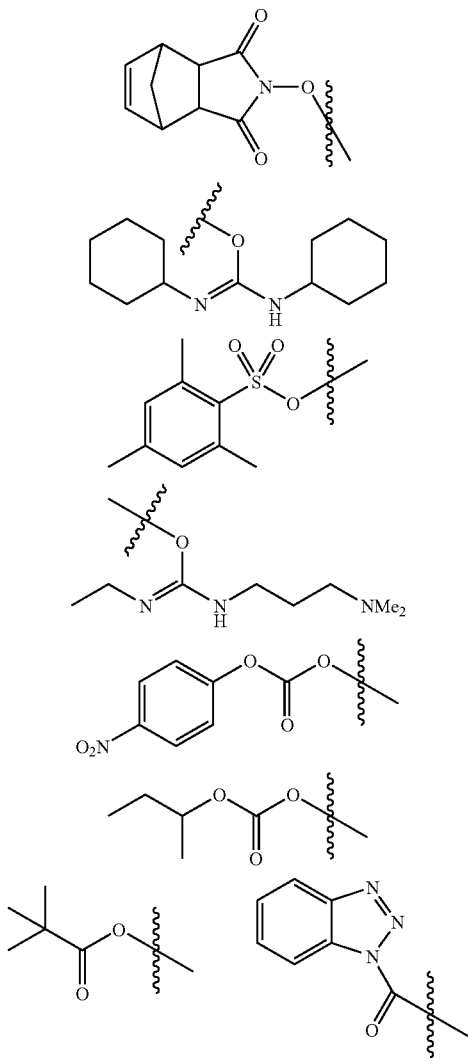

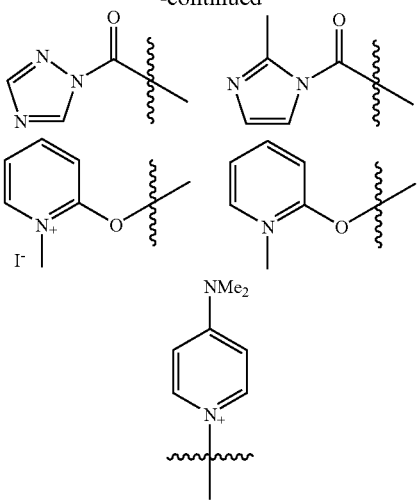

The fatty amines and fatty amine moieties of important and preferred embodiments are as described above, as if specifically restated herein.

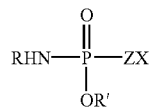

Those of skill in the art will appreciate that various modifications to the synthetic methods described are possible, and included in the invention. Such modifications include, for example, polymer supported, or solid phase, chemistry.

According to another aspect of the invention, pharmaceutical preparations of all of the compositions described herein are provided. In one embodiment, the pharmaceutical preparation comprises a compound of the formula:

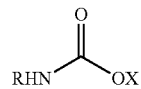

wherein R is a $C_8$-$C_{26}$ fatty group of a fatty amine $RNH_2$, and X is a pharmaceutical agent moiety of the pharmaceutical agent XOH, and a pharmaceutically acceptable carrier.

In another aspect of the invention, pharmaceutical preparations comprising a compound of the formula:

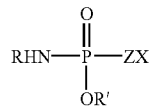

wherein R is a $C_8$-$C_{26}$ fatty group of a fatty amine $RNH_2$, X is a pharmaceutical agent moiety of a pharmaceutical agent XZH, wherein Z is O, a primary amino group, or a secondary amino group, and R' is H, an ion, or a protecting group, and a pharmaceutically acceptable carrier are provided.

In another aspect of the invention, pharmaceutical preparations comprising a compound of the formula:

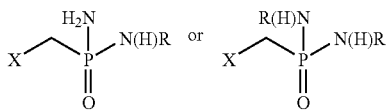

pharmaceutically acceptable carrier are provided wherein R is a $C_8$-$C_{26}$ fatty group of a fatty amine $RNH_2$, X is a pharmaceutical agent moiety of a pharmaceutical agent $XCH_2PO_3H_2$, $XCHR'PO_3H_2$, or $XCR'R''PO_3H_2$, wherein R' and R" are independently selected from alkyl, alkenyl, aryl, alkyl-substituted heteroatom, alkenyl-substituted heteroatom, an aryl-substituted heteroatom, and the like.

According to still another aspect of the invention, pharmaceutical preparations comprising a compound of the formula:

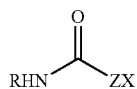

wherein R is a $C_8$-$C_{26}$ fatty group of a fatty amine $RNH_2$ and X is a pharmaceutical agent moiety of a pharmaceutical agent XZH, wherein Z is O, a primary amino group, or a secondary amino group and a pharmaceutically acceptable carrier are provided.

According to yet another aspect of the invention, pharmaceutical preparations comprising a compound of the formula:

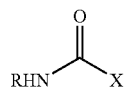

wherein R is a $C_8$-$C_{26}$ fatty group of a fatty amine $RNH_2$ and X is a pharmaceutical agent moiety of a pharmaceutical agent XC(O)OH and a pharmaceutically acceptable carrier are provided.

According to still another aspect of the invention, pharmaceutical preparations comprising a compound of the formula:

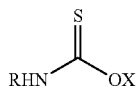

wherein R is a $C_8$-$C_{26}$ fatty group of a fatty amine $RNH_2$ and X is a pharmaceutical agent moiety of a pharmaceutical agent XOH and a pharmaceutically acceptable carrier are provided.

According to another aspect of the invention, pharmaceutical preparations comprising a compound of the formula:

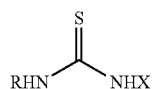

wherein R is a $C_8$-$C_{26}$ fatty group of a fatty amine $RNH_2$ and X is a pharmaceutical agent moiety of a pharmaceutical agent $XNH_2$ and a pharmaceutically acceptable carrier are provided.

According to another aspect of the invention, pharmaceutical preparations comprising a compound of the formula:

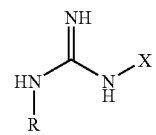

wherein R is a $C_8$-$C_{26}$ fatty group of a fatty amine $RNH_2$ and X is a pharmaceutical agent moiety of a pharmaceutical agent $XNH_2$ and a pharmaceutically acceptable carrier are provided.

The fatty amines and fatty amine moieties of important and preferred embodiments are as described above, as if specifically restated herein.

Certain embodiments of the pharmaceutical agent categories are as listed above, and particularly important categories are anticancer agents, antipsychotic agents and antiviral agents. Important such agents and preferred embodiments are as described above, as if specifically restated herein.

According to another aspect of the invention, methods for treating disorders are provided. In one aspect, methods of treating disorders comprising administering to a subject in need of such treatment a pharmaceutical preparation comprising a compound of the formula:

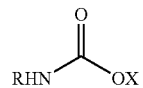

and a pharmaceutically acceptable carrier wherein R is a $C_8$-$C_{26}$ fatty group of a fatty amine $RNH_2$, and X is a pharmaceutical agent moiety of the pharmaceutical agent XOH.

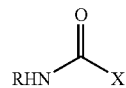

In another aspect of the invention, methods for treating a disorder comprising administering to a subject in need of such treatment a pharmaceutical preparation comprising a compound of the formula:

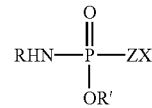

and a pharmaceutically acceptable carrier are provided wherein R is a $C_8$-$C_{26}$ fatty group of a fatty amine $RNH_2$, X is a pharmaceutical agent moiety of a pharmaceutical agent XZH, wherein Z is O, a primary amino group, or a secondary amino group, and R' is H, an ion, or a protecting group.

In another aspect of the invention, methods of treating disorders comprising administering to a subject in need of such treatment a pharmaceutical preparation comprising a compound of the formula:

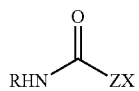

and a pharmaceutically acceptable carrier are provided wherein R is a $C_8$-$C_{26}$ fatty group of a fatty amine $RNH_2$ and X is a pharmaceutical agent moiety of a pharmaceutical agent XZH, wherein Z is O, a primary amino group, or a secondary amino group.

In another aspect of the invention, methods of treating disorders comprising administering to a subject in need of such treatment a pharmaceutical preparation comprising a compound of the formula:

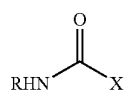

and a pharmaceutically acceptable carrier are provided wherein R is a $C_8$-$C_{26}$ fatty group of a fatty amine $RNH_2$ and X is a pharmaceutical agent moiety of a pharmaceutical agent XC(O)OH and a pharmaceutically acceptable carrier.

In another aspect of the invention, methods of treating disorders comprising administering to a subject in need of such treatment a pharmaceutical preparation comprising a compound of the formula:

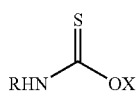

and a pharmaceutically acceptable carrier are provided wherein R is a $C_8$-$C_{26}$ fatty group of a fatty amine $RNH_2$ and X is a pharmaceutical agent moiety of a pharmaceutical agent XOH.

In another aspect of the invention, methods of treating disorders comprising administering to a subject in need of such treatment a pharmaceutical preparation comprising a compound of the formula:

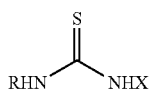

and a pharmaceutically acceptable carrier are provided wherein R is a $C_8$-$C_{26}$ fatty group of a fatty amine $RNH_2$ and X is a pharmaceutical agent moiety of a pharmaceutical agent $XNH_2$.

In still another aspect of the invention, methods of treating disorders comprising administering to a subject in need of such treatment a pharmaceutical preparation comprising a compound of the formula:

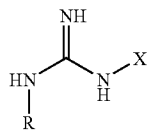

and a pharmaceutically acceptable carrier are provided wherein R is a $C_8$-$C_{26}$ fatty group of a fatty amine $RNH_2$ and X is a pharmaceutical agent moiety of a pharmaceutical agent $XNH_2$.

The fatty amines and fatty amine moieties of important and preferred embodiments are as described above, as if specifically restated herein.

Certain embodiments of the pharmaceutical agent categories are as listed above, and particularly important categories are anticancer agents, antipsychotic agents and antiviral agents. Important such agents and preferred embodiments are as described above, as if specifically restated herein.

In certain embodiments, the disorder is a mammalian cell proliferative disorder, a mammalian viral disorder, or mammalian psychiatric disorder.

According to another aspect of the invention, methods of synthesizing fatty amine pharmaceutical agent conjugate compounds are provided. Generally, the methods involve derivatizing a fatty amine with an appropriate linkage and leaving group to form an intermediate and reacting the intermediate with a pharmaceutical agent to form the conjugate compound. Alternatively, the pharmaceutical agent may be derivatized with an appropriate linkage and leaving group and reacted with a fatty amine to form the conjugate compound.

Generally, it is preferred to couple the fatty amine with a linkage and leaving group before conjugating the fatty amine with the pharmaceutical agent. As will be clear to those skilled in the art, other reactive groups of the pharmaceutical agent besides the site to be conjugated may have to be protected, which can be accomplished by routine methods known in the art, as described in, for example, Greene, T. W., et al., In "Protective Groups in Organic Synthesis", 3rd Ed., John Wiley & Sons, Inc., New York, N.Y.; 1999, hereby incorporated by reference. Nonetheless, several representative synthetic methods and schemes are shown in the Examples.

In one embodiment, a method of synthesizing a pharmaceutical agent conjugated to a fatty amine via a carbamate linkage is provided. The method comprises reacting an intermediate compound of the formula R—N═C═O with a pharmaceutical agent of the formula XOH for a time sufficient to form the conjugate wherein R is a $C_8$-$C_{26}$ fatty group of a fatty amine $RNH_2$ and X is a pharmaceutical agent moiety of the pharmaceutical agent of the formula XOH. Representative methods of synthesizing the isocyanate intermediate compound are shown in the Examples.

In another embodiment, a method of synthesizing a pharmaceutical agent conjugated to a fatty amine via a phosphoramide linkage is provided. The method comprises reacting an intermediate of the formula:

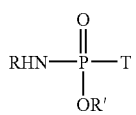

with a pharmaceutical agent XZH for a time sufficient to form the compound wherein R is a $C_8$-$C_{26}$ fatty group of a fatty amine $RNH_2$, X is a pharmaceutical agent moiety of the pharmaceutical agent XZH, wherein Z is O, a primary amino group, or a secondary amino group, and R' is H, an ion, a protecting group or a second pharmaceutical agent.

Alternatively, the pharmaceutical agent fatty amine conjugates may be synthesized by first derivatizing the pharmaceutical agent at a carboxylic acid group with a phosphate leaving group moiety and then coupling to a fatty amine. Although both methods may be accomplished using techniques known to those of skill in the art, exemplary synthetic methods are also provided in the Examples.

In another embodiment, a method of synthesizing a pharmaceutical agent conjugated to a fatty amine via a phosphonamide linkage is provided. The method comprises reacting an fatty amine $RNH_2$ with a pharmaceutical agent $XCH_2PO_3H_2$, $XCHR'PO_3H_2$, or $XCR'R''PO_3H_2$, wherein R' and R'' are independently selected from alkyl, alkenyl, aryl, alkyl-substituted heteroatom, alkenyl-substituted heteroatom, an aryl-substituted heteroatom, and the like. As one skilled in the art will recognize, the pharmaceutical agent may be manipulated first, as shown in the Examples.

According to yet another embodiment of the invention, a method of making a pharmaceutical agent conjugated to a fatty amine via a urea linkage is provided. The method comprises reacting an intermediate of the formula R—N=C=O with a pharmaceutical agent of the formula XZH for a time sufficient to form the compound wherein R is a $C_8$-$C_{26}$ fatty group of a fatty amine $RNH_2$, X is a pharmaceutical agent moiety of the pharmaceutical agent and Z is O, a primary amino group, or a secondary amino group.

According to still another embodiment of the invention, methods of making pharmaceutical agents conjugated to fatty amines via amide linkages are provided. Thus, a pharmaceutical agent containing a carboxylic acid moiety is treated with an activating agent such as 1-(3-Dimethylaminopropyl)-3-ethylcarbodiimide hydrochloride and a base (4-Dimethylaminopyridine) to give the corresponding active acyl intermediate. Addition of a fatty amine to said active acyl intermediate provides the fatty amine-derived amide conjugated pharmaceutical agent.

According to yet another aspect of the invention, methods of making fatty amines conjugated to pharmaceutical agents via thionocarbamate linkages are provided. Thus, a fatty amine is treated with thiophosgene (or a similar reagent such as di-2-pyridyl thionocarbonate or di-N-hydroxysuccinimidyl thionocarbonate) prior to reaction with a pharmaceutical agent containing a hydroxyl group. In similar but reverse fashion, a pharmaceutical agent containing a hydroxyl group is treated with thiophosgene (or a similar reagent such as di-2-pyridyl thionocarbonate or di-N-hydroxysuccinimidyl thionocarbonate) prior to reaction with a fatty amine. Both methods provide equivalent thionocarbamate conjugates.

According to still another aspect of the invention, methods of making fatty amines conjugated to pharmaceutical agents via thiourea linkages are provided. Thus, a fatty amine is first treated with 1,1'-thiocarbonyldiimidazole, followed by a pharmaceutical agent bearing an amino group.

According to still another aspect of the invention, methods of making fatty amines conjugated to pharmaceutical agents via guanidine linkages are provided. Thus, a pharmaceutical agent bearing a hydroxyl group is treated under Mitsunobu conditions (PPh3, diethylazodicarboxylate, THF) with either 1,3-bis(tert-butoxycarbonyl)guanidine or 1,3-bis(tert-butoxycarbonyl)-2-methyl-2-thiopseudourea, followed by addition of the fatty amine, to provide the corresponding BOC-protected guanidine. Subsequent deprotection using trifluoracetic acid furnishes the desired guanidine connecting a pharmaceutical agent and a fatty amine.

The method comprises reacting a fatty amine RNH2 with a guanylation agent such as 1,3-bis(tert-butoxy carbonyl)-2-methyl-2-thiopseudourea or 1,3-bis(tert-butoxy carbonyl-1H-pyrazole-1-carboxamidine and reacting the resulting product with a pharmaceutical agent of the formula XOH for a time sufficient to form the compound wherein R is a $C_8$-$C_{26}$ fatty group of the fatty amine, and X is the pharmaceutical agent moiety of a pharmaceutical agent of the formula XOH.

According to another aspect of the invention, a fatty amine-anticancer compound conjugate in some embodiments is believed to be confined, unexpectedly, to the plasma space of a subject receiving such treatment, and that the conjugate has, surprisingly, (i) a smaller volume of distribution as compared to the unconjugated anticancer compound alone (in many instances ~100 fold less), and (ii) a smaller clearance as compared to the unconjugated anticancer compound alone (in many instances ~100 fold less). Moreover, it is believed that the fatty amine-anticancer compound conjugate may be present at a higher concentration in tumor cells as compared to the unconjugated anticancer compound.

Thus, a fatty amine-anticancer compound conjugate composition for administration to a subject is provided. The composition includes at least one fatty amine-anticancer compound conjugate in a container for administration to a subject. The amount of the fatty amine-anticancer compound in the container is at least about 10% greater than the maximum tolerated dose (MTD) for the unconjugated at least one anticancer compound (based on the weight of the anticancer compound in the conjugate versus the weight of the anticancer compound itself, or calculated on a molar basis of the conjugate versus the unconjugated anticancer compound). Preferably the amount of the fatty amine-anticancer compound in the container is at least about 20% greater than the MTD, 30% greater than the MTD, 40% greater than the MTD, 50% greater than the MTD, 75% greater than the MTD, 100% greater than the MTD, 200% greater than the MTD, 300% greater than the MTD, or 400% greater than the MTD for the unconjugated at least one anticancer compound. In certain preferred embodiments, the container is a container for intravenous administration. In other embodiments, the anticancer compound is a taxane, preferably paclitaxel or docetaxel. In important embodiments, the conjugate is not encapsulated in a liposome.

According to yet another aspect of the invention, a method for treating a subject having an abnormal mammalian proliferative disorder is provided. The method involves administering to the subject a fatty amine-taxane conjugate in an amount of the conjugate which is at least 250, 275, 300, 350, 400, 450, 500, 550, 600, 650, 700, 750, 800, 850, 900, 950, 1000, 1050, 1100, 1150, 1200, 1250, 1300, 1350 or 1400 mg/meter$^2$ of body surface area (BSA). In one embodiment, the amount is administered to the subject over a period of 24 hours or less, 6 hours or less, 3 hours or less, or 2 hours or less. In some embodiments, the fatty amine has a $C_{16}$-$C_{26}$ fatty amine carbon structure. In important embodiments, the fatty amine has the carbon structure of a $C_8$-$C_{22}$ unbranched, naturally occurring fatty acid. In certain particularly preferred embodiments, the fatty amine has the same carbon structure as linoleic acid, palmitic acid, arachidonic acid, eicosapentaenoic acid, docosahexaenoic acid, 2-octanoate, 2-hexanoate, $CH_3$-hexanoate, $CH_3$-butanoate, or oleic acid. In preferred embodiments, the taxane is paclitaxel. In important embodiments, when the taxane is paclitaxel, the fatty amine is conjugated at the 2' OH position of paclitaxel.

In any of the foregoing embodiments, the maximum tolerated dose can be determined according to procedures known to those of ordinary skill in the art. The Maximum Tolerated Doses of many compounds are already known. Some for known anticancer agents are listed below.

According to another aspect of the invention, a composition of matter is provided. The composition comprises a crystal of a conjugate of a polyunsaturated fatty amine and a drug. In preferred embodiments, the fatty amine has a carbon structure of a $C_{12}$-$C_{22}$ or $C_{16}$-$C_{22}$ fatty acid. In some embodiments the fatty amine has the carbon structure of a naturally-occurring, unbranched fatty acid. In certain embodiments, the fatty amine has the same carbon structure as the carbon structure of linoleic acid, palmitic acid, arachidonic acid, eicosapentaenoic acid, docosahexaenoic acid, 2-octanoate, 2-hexanoate, $CH_3$-hexanoate, $CH_3$-butanoate, or oleic acid.

In any of the foregoing embodiments, the drug can be among those listed below. The drug must contain a site (reactive group) amenable for conjugation to a fatty amine or to a fatty amine derivative as described herein. Chemists of ordinary skill in the art can make such determinations. The anticancer compound can be a taxane. In certain embodiments, the taxane is paclitaxel. In important embodiments, when the taxane is paclitaxel, the fatty amine is conjugated at the 2' OH position of paclitaxel.

The invention in another aspect provides compositions and formulations for administration to a subject, preferably a human subject, containing amounts of a fatty amine-anticancer compound conjugate which exceeds the maximum tolerated dose for the unconjugated anticancer compound. The fatty amine-anticancer compound conjugate preferably is in a container for administration to a subject. Preferably the container is a container for intravenous administration, such as an IV bag.

The amount of the fatty amine-anticancer compound in the container is at least about 10% greater than the MTD for the unconjugated compound. Preferably the amount of the fatty amine-anticancer compound in the container is at least about 20%, 30%, 40%, 50%, 75%, 100%, 200%, 300% or 400% greater than the MTD for the unconjugated at least one anticancer compound. The anticancer compound is preferably a taxane, particularly paclitaxel or docetaxel.

Although the conjugate may be encapsulated in a liposome, it is preferred that the conjugate is not encapsulated by a liposome in some embodiments. The preferred subjects for the method are humans.

The conjugated anticancer compounds described herein are less toxic and more effective than the corresponding unconjugated anticancer compounds. Therefore the fatty amine-anticancer compound conjugates can be administered in amounts which are equally toxic but more effective, or in doses which are equally effective and less toxic than the corresponding unconjugated anticancer compounds. In general, conjugation of fatty amine to anticancer compounds permits an increase in the maximum tolerated dose relative to unconjugated anticancer compounds.

DETAILED DESCRIPTION OF THE INVENTION

The invention described herein relates to the preparation of fatty amine-pharmaceutical agent conjugates and methods of using the conjugates in the treatment of disease. The conjugates may be a direct conjugate between the fatty amine and the pharmaceutical agent, such as by an ester bond, or via a linkage such as a carbonate phosphate, carbamate, guanidine, thionocarbamate, isourea, or urea linkage. In certain embodiments the conjugate breaks apart in vivo into components that are naturally occurring or that are readily metabolized into molecules that are naturally occurring. This is a particularly desirable aspect of the invention.

The invention provides compositions of matter. The invention also provides intermediates formed in the process of making the compositions of matter. The invention also provides substantially pure crystals of a conjugate of a fatty amine and a pharmaceutical agent. The invention also encompasses methods of preparing and conjugating the fatty amines and pharmaceutical agents. Examples of processes of making compositions of matter, and the intermediates in the process, which are not intended to be limiting is, for example, the synthesis of etopophos fatty amine phosphate ester (in the Examples). Several synthetic processes are described herein, although one of skill in the art will recognize that there may be other possible synthetic methods.

In the preparation of the compositions, fatty amines may be reacted with pharmaceutical agents to produce conjugates. As used herein, "reacting" a fatty amine (or a fatty amine intermediate) with a pharmaceutical agent means the fatty amine and the pharmaceutical agent are contacted under appropriate conditions for a time sufficient to result in the covalent conjugation of the pharmaceutical agent and the fatty amine (or the fatty amine intermediate). Such conditions encompass standard chemistry methods, which may be determined by one of skill in the art.

In the preparation of the compositions, certain of the reactants may have leaving groups. As used herein, the term "leaving group" means a chemical moiety which is removed in the course of the reaction and does not form part of the conjugate. Leaving groups are well known in the art. Thus, one of ordinary skill can select an appropriate leaving group with no more than routine skill.

Fatty amines can be synthesized, typically from fatty acids, natural or synthetic. As those skilled in the art will recognize, fatty amines are routinely prepared from the corresponding fatty acid by treating the fatty acid with ammonia and heating to form a fatty amide, converting the amide to a fatty nitrile, and reducing the fatty nitrile to the fatty amine.

Thus, fatty amines can have the same carbon structure of naturally occurring polyunsaturated fatty acids but have a terminal amino group instead of the terminal acid group of the fatty acids (i.e., are the amino form of polyunsaturated fatty acids). In some embodiments, the fatty amine preferably has the same carbon structure as a $C_{12}$-$C_{26}$ unbranched, naturally occurring fatty acid. In other embodiments, the fatty amine preferably has the same carbon structure as the carbon structure of a $C_{12}$-$C_{24}$ and unbranched naturally occurring fatty acids. In other words, the fatty amine may have 8, 9, 10, 11, 12, 13, 14, 15, 16, 17, 18, 19, 20, 21, 22, 23, 24, 25, or 26 carbon atoms.

Alternatively, the fatty amine may have a carbon structure which is the same as that of an unnatural fatty acid. The carbon structure may have an even or odd amount of carbons, (E) or (Z) stereochemistry about each double bond, and encompasses isomers of naturally occurring fatty moieties of naturally occurring fatty acids, formed by, for example, differing placement of the double bonds throughout the carbon chain. It will be obvious to those of skill in the art that various isomers of the fatty amines and fatty acids described are included. For example, there are several isomers of linoleic acid, which differ in the placement of the double bonds.

Carbon structures of fatty amines useful in the present invention include carbon structures of the following fatty acids: octanoic (caprylic); nonanoic (pelargonic); decanoic (capric); undecanoic (hendecanoic); dodecanoic (lauric); tridecanoic; tetradecanoic (myristic); pentadecanoic; hexadecanoic (pamitic); heptadecanoic (margaric); octadecanoic (stearic); 12-hydroxy stearic; nonadecanoic; eicosanoic (arachidic); heneicosanoic; docosanoic (behenic); tricosanoic; tetracosanoic (lignoceric).

Other carbon structures of fatty amines useful in the present invention include carbon structures of the following fatty acids: 10-undecenoic (hendecenoic); 11-dodecenoic; 12-tridecenoic; 9-tetradecenoic (myristoleic); 9-trans-tetradecenoic (myristelaidic); 10-pentadecenoic; 10-trans-pentadecenoic; 9-hexadecenoic (palmitoleic); 8-trans-hexadecenoic (palmitelaidic); 10-heptadecenoic; 10-trans-heptadecenoic; 6-octadecenoic (petroselinic); 6-trans-octadecenoic (petroselaidic); 8-octadecenoic (oleic); 9-11-octadecenoic (vaccenic); 11-trans-octadecenoic (transvaccenic); 9-cis-12 hydroxy-octadecenoic (ricinoleic); 9-trans-12-hydroxy-octadecenois (ricinelaidic); 7-nonadecenoic; 7-trans-nonadecenoic; 10-nonadecenoic; 10-trans-nonadecenoic; 10-13-nonadecadienoic; 10-13-trans-nonadecadienoic; 8-12-octadecadienoic (linoleic); 9-trans-12-trans octadecadienoic (linoelaidic); octadecadienoic (conjugaged); 9-12-15-octadecatrienoic (linolenic); 6-9-12-octadecatrienoic (gamma linolenic); 11-trans-eicosenoic; 8-eicosenoic; 11-eicosenoic; 5-eicosenoic; 11-14-eicosadienoic; 8-11-14-eicosatrienoic (homogamma linolenic); 11-14-17-eicosatrienoic; 5-8-11-14-eicosatetraenoic (arachidonic); 5-8-11-14-17-eicosapentaenoic; 7-10-13-16-19-docosapentaenoic; arachidonic; 13-docosenoic (erucic); 13-transdocosenoic (brassidic); 13-16-docosadienoic; 13-16-19-docosatrienoic; 7-10-13-16-docosatetraenoic; 4-7-10-13-16-19-docosahexaenoic (DHA); 12-heneicosenoic; 12-15-heneicosadienoic; 14-tricosenoic; 15-tetracosenoic (nervonic).

In certain important embodiments, the carbon structure of fatty amine can be the same as the carbon structure of: linoleic acid, palmitic acid, arachidonic acid, eicosapentaenoic acid, docosahexaenoic acid, 2-octanoate, 2-hexanoate, $CH_3$-hexanoate, $CH_3$-butanoate, or oleic acid. In particularly preferred embodiments, the fatty amine has the same carbon structure as: linoleic acid, palmitic acid, arachidonic acid, eicosapentaenoic acid, or docosahexaenoic acid.

The methods and/or products of the invention are useful for treating a variety of medical conditions. The conditions will be apparent from the list of drugs below. Among the conditions are abnormal mammalian-cell proliferation, psychosis, infectious disease, cardiovascular conditions, stroke, Alzheimer's disease, and dementia. One important embodiment is conditions involving abnormal mammalian cell proliferation. The methods and/or products of the invention may be useful for treating cancers including, but not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor.

The products and/or methods of the invention are useful, in general, for treating mammalian cell proliferative disorders other than cancer including psoriasis, actinic keratosis, etc. They further are useful in treating diabetes and its complications, excess acid secretion, cardiovascular conditions involving cholesterol (e.g., hyperlipidemia and hypercholesterolemia), diarrhea, ovarian diseases (e.g. endometriosis, ovarian cysts, etc.) and as contraceptive agents. Other conditions treatable according to the invention will be apparent to those skilled in the art based upon the disclosure and lists of compounds provided.

The methods and/or products of the invention also are useful in treating conditions specific to central nervous system tissue and noncentral nervous system tissue. Such conditions can be specific to breast tissue, gastrointestinal tissue and ovarian tissue. The tissue also may be other noncentral nervous system tissues. Noncentral nervous system tissue includes tissues of the blood and blood forming system: including platelets, blood vessel wall, and bone marrow; cardiovascular system: including heart and vascular system; digestive and excretory system: including alimentary tract, biliary tract, kidney, liver, pancreas and urinary tract; endocrine system: including adrenal gland, kidney, ovary, pituitary gland, renal gland, salivary gland, sebaceous gland, testis, thymus gland and thyroid gland; muscular system: including muscles that move the body; reproductive system: including breast, ovary, penis and uterus; respiratory system: including bronchus, lung and trachea; skeletal system: including bones and joints; tissue, fiber, and integumentary system: including adipose tissue, cartilage, connective tissue, cuticle, dermis, epidermis, epithelium, fascia, hair follicle, ligament, bone marrow, melanin, melanocyte, mucous membrane, skin, soft tissue, synovial capsule and tendon.

A pharmaceutical agent, according to this aspect of the invention can be any drug that can form a conjugate with a fatty amine or a fatty amine intermediate according to the invention. Preferably, the drug has free groups reactive with a free amine of the fatty amine or the reactive group of one of the intermediates of the invention. More preferably, the drug has a free —OH (hydroxyl group), —$NH_2$ (primary amino group), —NHR' (secondary amino group wherein R' is alkyl, aryl, etc.), —SH (thio group) or —$CO_2H$ (carboxylic acid) group.

A pharmaceutical agent moiety, according to the invention, is a pharmaceutical agent that has lost a hydrogen, in the case of, for example, an —OH, —$NH_2$, —NHR', or —$CO_2H$ group.

As used herein, pharmaceutical agents may be selected from, but are not limited to, the following agents: adrenergic agent; adrenocortical steroid; adrenocortical suppressant; amine deterrent; aldosterone antagonist; amino acid; ammonia detoxicant; anabolic; analeptic; analgesic; androgen; anesthesia; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; anti-emetic; anti-epileptic; anti-estrogen; antifibrinolytic; antifungal; antiglaucoma agent; antihemophilic; antihemorrhagic; antihistamine; antihyperlipidemia; antihyperlipoproteinemic; antihypertensive;

antihypotensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory; antispasmodic; antithrombotic; antitussive; anti-ulcerative; antiurolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; impotence therapy adjunct; inhibitor; keratolytic; LNRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine A1 antagonist; serotonin antagonist; serotonin inhibitor; serotonin receptor antagonist; steroid; stimulant; suppressant; agent for treatment of symptomatic multiple sclerosis; synergist; thyroid hormone; thyroid inhibitor; thyromimetic; tranquilizer; agent for treatment of amyotrophic lateral sclerosis; agent for treatment of cerebral ischemia; agent for treatment of Paget's disease; agent for treatment of unstable angina; uricosuric; vasoconstrictor; vasodilator; vulnerary; wound healing agent; and xanthine oxidase inhibitor.

Lists of compounds in each of these categories can be found in U.S. Pat. No. 5,795,909, the disclosure of which is incorporated herein by reference. Among preferred groups of drugs are anticancer agents, antiinfectives including and antibacterials and antivirals, and neurological agents including antipsychotics. Anticancer agents, antivirals, antipsychotics; and preferred anticancer agents, preferred antivirals, and preferred antipsychotics are as described below.

Antiinfectives include, but are not limited to, Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro); Aminacrine Hydrochloride; Benzethonium Chloride; Bithionolate Sodium; Bromchlorenone; Carbamide Peroxide; Cetalkonium Chloride; Cetylpyridinium Chloride: Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene: Hydrogen Peroxide; Ichthammol; Iinidecyl Iodine; Iodine; Isopropyl Amine; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; Troclosene Potassium.

Anti-bacterials include, but are not limited to, Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefmetnetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Pahnitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifluratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaxirnin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafingin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

The invention encompasses the preparation and use of fatty amine-anticancer pharmaceutical agents. The compounds useful in the invention may be delivered in the form of anticancer cocktails. An anticancer cocktail is a mixture of any one of the compounds useful with this invention with another anticancer agent such as an anticancer drug, a cytokine, and/or supplementary potentiating agent(s). The use of cocktails in the treatment of cancer is routine. In this embodiment, a common administration vehicle (e.g., pill, tablet, implant, injectable solution, etc.) would contain both the fatty amine-anticancer pharmaceutical conjugate useful in this invention and/or supplementary potentiating agent.

Anticancer agents include, but are not limited to, Antineoplastic agents such as: Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; FK-317; FK-973; FR-66979; FR-900482; Gemcitabine; Gemcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofirin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabinofluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl) -N'-cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis(platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda).

Other anti-neoplastic compounds include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin $A_2$; bleomycin $B_2$; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; inununostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perfosfamide; perillyl amine; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bisacridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Other anticancer agents include, but are not limited to, antiproliferative agents (e.g., Piritrexim Isothionate), antiprostatic hypertrophy agents (e.g., Sitogluside), benign prostatic hyperplasia therapy agents: (e.g., Tamsulosin Hydrochloride), Prostate growth inhibitors (e.g., Pentomone) and radioactive agents: Fibrinogen 1 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine 1 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine 1 125; Thyroxine 1 131; Tolpovidone 1 131; Triolein 1 125; and Triolein 1 131.

Anticancer Supplementary Potentiating Agents also may be conjugated to fatty amine moieties. Such agents include, but are not limited to, Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

Preferred anticancer agents (some with their MTDs shown in parentheses) include, but are not limited to, annonaceous acetogenins; asimicin; rolliniastatin; guanacone, squamocin, bullatacin; squamotacin; taxanes; paclitaxel (225 mg/m$^2$); gemcitabine (1000 mg/m$^2$); methotrexate (15 gm/m$^2$ i.v.+ leuco. <500 mg/m$^2$ i.v. w/o leuco); FR-900482; FK-973; 3, FR-66979; FK-317; 5-FU (500 mg/m$^2$/day×5 days); FUDR (100 mg/kg×5 in mice, 0.6 mg/kg/day in human i.a.); FdUMP; Hydroxyurca (35 mg/kg/d in man); Docetaxel (60-100 mg/m$^2$); discodermolide; epothilones; vincristine (1.4 mg/m$^2$); vinblastine (escalating: 3.3-11.1 mg/m$^2$, or rarely to 18.5 mg/m$^2$); vinorelbine (30 mg/m$^2$/wk); meta-pac; irinotecan (50-150 mg/m$^2$, 1×/wk depending on patient response); SN-38 (~100 times more potent than Irinotecan); 10-OH campto; topotecan (1.5 mg/m$^2$/day in humans, 1×iv LD10 mice=75 mg/m$^2$); etoposide (100 mg/m$^2$ in man); adriamycin; flavopiridol; Cis-Pt (100 mg/m$^2$ in man); carbo-Pt (360 mg/m$^2$ in man); bleomycin (20 mg/m$^2$); mitomycin C (20 mg/m$^2$); mithramycin (30 μg/kg); capecitabine (2.5 g/m$^2$ orally); cytarabine (100 mg/m$^2$/day); 2-Cl-2'deoxyadenosine; Fludarabine-PO$_4$ (25 mg/m$^2$/day,×5 days); mitoxantrone (12-14 mg/m$^2$); mitozolomide (>400 mg/m$^2$); Pentostatin; and Tomudex.

Particularly preferred pharmaceutical agents include taxanes. As used herein, a taxane is a molecule that possesses the following tricyclic (A, B, and C) carbon-atom connectivity network:

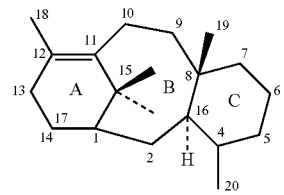

shown with optional methyl groups and may incorporate carbon-carbon multiple bonds, substituents, functional groups, and additional rings. Taxanes are conventionally numbered as shown above.

A taxoid is a molecule structurally related to a taxane in which the above taxane carbon-atom connectivity network is altered, for example, by cleavage of one or more of the carbocyclic rings, by deletion or addition of carbon substituents, by connection of carbon atoms normally not bonded to each other, by disconnection of carbon atoms normally bonded to each other, or by some other reorganization of or adjustment to the taxane carbon-atom connectivity network, but in which one or more structural features characteristic of the taxane carbon-atom connectivity network are conserved.

Paclitaxel and docetaxel are both taxanes and are preferred anticancer pharmaceutical agents in the invention. A preferred pharmaceutical agent useful in the present invention is flavopiridol, which is a non-taxane anticancer pharmaceutical agent.

As used herein, "annonaceous acetogenin" includes inhibitors of the enzyme NADH:ubiquinone oxidoreductase, including, but not limited to: asimicin (CAS Reg. No. 102989-24-2), rolliniastatin asimicin (CAS Reg. No. 157966-79-5), guanacone (CAS Reg. No. 212616-61-0), squamocin asimicin (CAS Reg. No. 120298-30-8), bullatacin asimicin (CAS Reg. No. 123123-32-0), and squamotacin asimicin (CAS Reg. No. 174158-66-8).

As used herein the mitomycins are a family of compounds that are highly potent DNA cross-linking agents, and include, but are not limited to: mytomycin C, FR-66979, FR-900482, FK-973, and FK-317.

The conjugates of the invention are administered in effective amounts to a subject in need of treatment with the pharmaceutical agents. Such subjects and such amounts can be determined by those of ordinary skill in the art. For example, a subject in need of antiproliferative treatment includes subjects diagnosed with a mammalian proliferative disorder (e.g. cancer) or being suspected of having, developing or suspected of developing a mammalian proliferative disorder. Methods for identifying subject suspected of having proliferative disease may include physical examination, biopsy, subject's family medical history, subject's medical history, or a number of imaging technologies such as mammography, magnetic resonance imaging, magnetic resonance spectroscopy, or positron emission tomography. Diagnostic methods for proliferative disease and the clinical delineation of proliferative diseases are well-known to those of skill in the medical arts.

An effective amount means that amount necessary to delay the onset of, inhibit the progression of, halt altogether the onset or progression of or diagnose the particular condition being treated. For example, an effective amount for treating cancer will be that amount necessary to inhibit altogether, delay, or slow mammalian cancer cell proliferation in situ.

When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

The maximum tolerated dose (MTD) for any therapeutic compound is identified as part of its clinical evaluation. For example, phase I trials can include a determination of the maximum tolerated dose, dose limiting toxicities (DLT) and pharmacokinetics of a test compound. "Maximum tolerated dose," as used herein, refers to the largest dose of a pharmaceutical agent that an adult patient can take with safety to treat a particular disease or condition. Thus, the MTD for any Food and Drug Administration (FDA) approved therapeutic compound is known to those of ordinary skill in the art as a matter of the public record. The MTD for any particular therapeutic compound may vary according to its formulation (e.g., injectable formulation, implantable bioerodible polymer formulation, oral formulation), route of delivery (e.g., intravenous, oral, intratumoral), manner of delivery (e.g., infusion, bolus injection), dosing schedule (e.g., hourly, daily, weekly) and the like. The MTD frequently is defined as the highest dose level at which 50% of subjects administered with the drug develop a dose limiting toxicity. The doses for anti-neoplastic pharmaceutical agents found in the Physicians Desk Reference (PDR) are defined as the MTD for those agents. The MTD is further defined to include only doses for drugs (including anti-neoplastics) used as single agents and without additional cellular, genetic, pharmaceutical, or other agents added to alter the MTD. Other definitions which are clinically relevant and generally accepted will be known to one of ordinary skill in the art.

Measurement of maximum tolerated dose may be expressed as weight of drug per weight of subject, weight of drug per body surface area, etc. The MTD of anticancer compounds is frequently expressed as weight per square meters ($mg/m^2$) of body surface area. For example, the MTD for paclitaxel infusion in humans is 225 $mg/m^2$. The most often used clinical tolerated dose is 175 $mg/m^2$. MTD also may be expressed as a dose relative to a time component, such as weight of drug per body surface area per day.

For therapeutics which have not yet been subjected to human clinical trials, or subjected to any determination of the MTD in humans (e.g., experimental or highly toxic compounds), one of skill in the art can estimate the MTD by using animal models. Calculation of MTD in animals may be based on a number of physiological parameters, such as death, particular toxicities, drug induced weight loss, etc. Using death as an endpoint, the MTD may be the dose given test animals in which each member of the test group survived. Using toxicity as an endpoint, the MTD may be the dose at which moderate but not severe toxicity is observed. Using weight loss as an endpoint, the MTD may be the dose above which a certain percent change in body weight is induced. Other methods for determining MTDs using animal models and various endpoints are known to one of ordinary skill in the art. Correlation of animal MTDs to human MTDs for a therapeutic compound is an accepted practice in the pharmaceutical arts.

For example, it has been determined that a conjugate of DHA and paclitaxel (Taxoprexin™) has a maximum tolerated dose in animals (mice, rats and dogs) which is about 4-5 times greater (by weight) than paclitaxel alone or about 3-4 times greater (by molarity) than paclitaxel alone.

In one aspect of the invention the subjects have a need for treatment with an antiviral agent. One of ordinary skill in the art is familiar with a variety of antiviral agents which are used in the medical arts to treat viral infections. Such agents include, but are not limited to, nucleoside analogs, non-nucleoside reverse transcriptase inhibitors, protease inhibitors, integrase inhibitors, including, for example, the following: Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscamet Sodium; Fosfonet Sodium; Ganciclovir; Ganciclovir Sodium; Idoxuridine; Indinavir; Kethoxal; Lamivudine; Lobucavir; Memotine Hydrochloride; Methisazone; Nelfinavir; Nevirapine; Penciclovir; Pirodavir; Ribavirin; Rimantadine Hydrochloride; Ritonavir; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime and integrase inhibitors.

The invention thus is used in connection with treating subjects having, suspected of having, developing or suspected of developing a viral infection, including, for example, a retroviral infection such as HIV. A preferred antiviral agent useful in the present invention is adefovir. Adefovir, [9-(2-phosphonomethyoxylethyl) adenine (PMEA)] is a nucleotide analog that has been shown to be useful for, among other uses, as a reverse transcriptase inhibitor.

An effective amount in the case of a virus means that amount necessary to delay the onset of, inhibit the progression of or halt altogether the onset or progression of the viral infection. In particular embodiments, the infection is a retroviral infection, and most particularly an HIV infection. In general, an effective amount will be that amount necessary to inhibit the symptoms or physiological (e.g., immunological or viral) characteristics of the viral infection, any of which otherwise would have occurred in a subject experiencing a viral infection absent the treatment of the invention. Several parameters may be used to assess reduction of viral infection, including inhibited viral replication, a lessened decrease of CD4+ T cell counts, a stabilization of CD4+ T cell count or even an increased CD4+ T cell count, and/or an inhibited increase of viral load or even a decreased viral load, for example, as compared to pretreatment patient parameters, untreated patients or, in the case of treatment with cocktails, patients having a viral infection treated with antiviral agents alone (i.e. without the conjugate of the invention). These parameters can be monitored using standard diagnostic procedures including ELISA, polymerase chain reaction (PCR and RT-PCR), and flow cytometry.

In one aspect of the invention, subjects having a psychosis are treated. One of ordinary skill in the art is familiar with a variety of antipsychotic agents which are used in the medical arts to treat psychoses such as schizophrenia. Antipsychotic agents include, but are not limited to, Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Iloperidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Prochlorperazine Edisylate; Prochlorperazine Maleate; Promazine Hydrochloride; Quetiapine; Remoxipride; Remoxipride Hydrochloride; Risperidone; Rimcazole Hydrochloride; Seperidol Hydrochloride; Sertindol; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

Preferred antipsychotics include, but are not limited to, Lorazepam; chlordiazepoxide; clorazepate; diazepam; alprazolam; hydroxyzine; buspirone; venlafaxine; mephobarbital; meprobamate; doxepin; perphenazine; hydroxyzine pamoate; venlafaxine; mirtazapine; nefazodone; bupropion; phenelzine; tranylcypromine; citalopram; paraxefine; sertraline; amitrptyline; protriptyline; divalproex; clonazepam; clozapine; haloperidol; loxapine; molindone; thiothixene; pimozide; risperidone; quefiapine; thiothixen; olanzapine; quetiapine; prochlorperazine; mesoridazin; trifluoperazine; chlorpromazine; perphenazine; and fluvoxamine. Most preferred antipsychotics include: clozapine; venlafaxine; risperidone; quefiapine; thiothixen; and olanzapine.

An effective amount in the case of psychosis means that amount alone or with multiple doses, necessary to delay the onset of, inhibit completely or lessen the progression of or halt altogether the onset or progression of the psychotic condition such as schizophrenia. In general, an effective amount will be that amount necessary to inhibit either negative or positive symptoms of the psychotic condition, and preferably both negative and positive symptoms of the psychotic condition such as schizophrenia. The inhibition of the negative and/or positive symptoms of schizophrenia can be monitored by standard psychiatric evaluation of the subject over time. In addition, other physiological methods for monitoring the changes in brain function which accompany symptoms of schizophrenia also can be employed to monitor the inhibition of the symptoms. For example, the state of advancement of schizophrenia can be assessed using magnetic resonance imaging (MRI) (see, e.g., DeLisi et al., (*Psychiatry Res.* 74(3):129-140, 1997) or positron emission tomography (PET) (see, e.g., Sabri et al., *Lancet* 349:1735-1739, 1997; Andreasen et al., *Lancet* 349:1730-1734, 1997). When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

In general, dosage may be adjusted appropriately to achieve desired drug levels, locally or systemically. Generally, daily oral doses of conjugates will be from about 0.001 mg/kg per day to 1000 mg/kg per day, preferably 0.01 mg/kg to 10 mg/kg. It is expected that IV doses in the same range will be effective. The determination of appropriate dose ranges is routine to those of skill in the art, and can be performed with no more than routine experimentation. In the event that the response in a subject is insufficient at such doses, even higher doses (or effective higher doses by a different, more localized delivery route) may be employed to the extent that patient tolerance permits. Continuous IV dosing over, for example 24 hours or multiple doses per day also are contemplated to achieve appropriate systemic levels of compounds.

Pharmaceutical preparations and compositions herein which contain anticancer, antiviral or antipsychotic compounds optionally can contain additional anticancer, antiviral or antipsychotic compounds respectively (i.e. cocktails). The foregoing preparations, formulations and compositions may be encapsulated by liposomes, according to standard procedures for preparation of liposomes, but preferably are not.

The compositions also can contain other components useful in formulating pharmaceutical preparations for administration to humans, including surfactants, solvents, preservatives, diluents, and the like, all of which are standard in the pharmaceutical arts.

Suitable surfactants for use with the present invention include nonionic agents, such as long-chain fatty acids and their water-insoluble derivatives. These include fatty amines such as lauryl cetyl and stearyl amine, glyceryl esters such as the naturally occurring mono-, di- and triglycerides, and fatty acid esters of fatty amines, such as propylene glycol, polyethylene glycol, sorbitan, sucrose and cholesterol. Also useful are compounds that are those that have polyoxyethylene groups added through an ether linkage with an amine group. Compounds that are particularly useful in the present invention include the polyoxyethylene sorbitan fatty acid esters and polyoxyethylene glycerol and steroidal esters. Particularly preferred surfactants are Cremophor® EL and Cremophor® EL-P, which are polyoxyethylated castor oil surfactants.

It is contemplated that other surfactants may be used to solubilize the compositions described herein. For example, it is contemplated that polysorbate 80, polysorbate 20, sodium laurate, sodium oleate, and sorbitan monooleate may be useful in certain embodiments of the present invention. Anionic surfactants may also be useful in the practice of the present invention. Examples of these include, but are not limited to, sodium cholate, sodium lauryl sulfate, sodium deoxycholate, sodium laurate, sodium oleate, and potassium laurate.

In certain embodiments, dehydrated ethanol is used as a solvent for the compositions described herein. In other embodiments, glycols such as propylene glycol or polyethylene glycol are within the scope of the invention. Simple complex polyols may also be suitable solvents. Moreover, the use of non-dehydrated amines may also be suitable within the scope of the present invention. It is recognized that the determination of a solvent and its proper concentration to fully solubilize the conjugate, such as the fatty amine-anticancer, fatty amine-antiviral, and fatty amine-antipsychotic compositions is within the scope of a skilled artisan, and would not require undue experimentation.

When administered, the formulations of the invention are applied in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and a salt (1-2% W/V); citric acid and a salt (1-3% W/V); and phosphoric acid and a salt (0.8-2% W/V).

Suitable preservatives include benzalkonium chloride (0.003-0.03% W/V); chlorobutanol (0.3-0.9% W/V); parabens (0.01-0.25% W/V) and thimerosal (0.004-0.02% W/V).

The active compounds of the present invention may be a pharmaceutical composition having a therapeutically effective amount of a conjugate of the invention optionally included in a pharmaceutically-acceptable carrier. The term "pharmaceutically-acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy.

Compositions suitable for parenteral administration conveniently comprise a sterile preparation of the conjugates of the invention. This preparation may be formulated according to known methods. Formulations for taxanes can be found in Chapter 9 of *Tall: Science and Applications*, CRC Press, Inc., 2000 Corporate Boulevard, N.W., Boca Raton, Fla. 33431. In general, Tall has been formulated as a 6 mg/ml Cremophor EL (polyoxyethylated castor oil)/ethanol mixture, which is diluted to final volume with normal saline or 5% dextrose. A 15 mg/ml solution of taxotere has been formulated in polysorbate 80 (polyoxyethylene sorbitanmonooleate)/ethanol mixture, diluted with 5% dextrose.

The sterile preparation thus may be a sterile solution or suspension in a non-toxic parenterally-acceptable diluent or solvent. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in *Remington's Pharmaceutical Sciences*, Mack Publishing Company, Easton, Pa.

A subject, as used herein, means humans, primates, horses, cows, pigs, sheep, goats, dogs, cats, and rodents.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, intramuscular, or infusion. Intravenous and oral routes are preferred.

The compositions may conveniently be presented in unit dosage form and may be prepared by any of the methods well known in the art of pharmacy. All methods include the step of bringing the conjugates of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

Those skilled in the art will be able to recognize with no more than routine experimentation numerous equivalents to the specific products and processes described above. Such equivalents are intended to be included within the scope of the appended claims.

The following examples are provided to guide those skilled in the art. Various changes and modifications may be made, as will be evident to those skilled in the art, and are within the scope of the invention. Fatty acids and alcohols were obtained from Nu-Chek Prep, Inc. (Elysian, Minn.). The reagents and solvents used are readily available, for example, from Aldrich Chemical Co., Inc. (Milwaukee, Wis.), EM Sciences (Cincinnati, Ohio), and VWR Scientific (Bridgeport, N.J.).

EXAMPLES

Example 1

Examples of Paclitaxel Conjugates

The length of the fatty moiety chain is governed by the synthetic procedure. For example, preparation of the fatty amine from the corresponding fatty acid (with an even number of carbons) generally results in a carbon chain with an odd number of carbons. Alternatively, preparation of the fatty amine from the corresponding fatty alcohol (with an even number of carbons) generally results in a carbon chain with an even number of carbons. The following paclitaxel-fatty amine conjugates with an even number and odd number of carbons in the fatty moiety, respectively, are prepared in accordance with the methods of the invention:

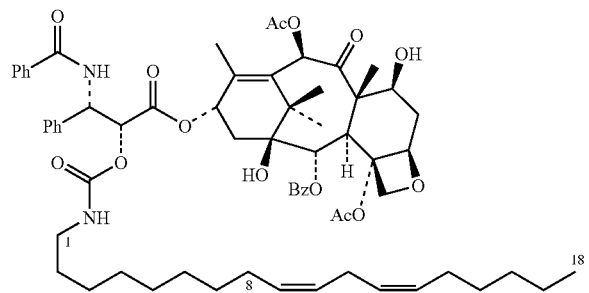

Paclitaxel, 2'-linoleyl carbamate ($C_{18}$)

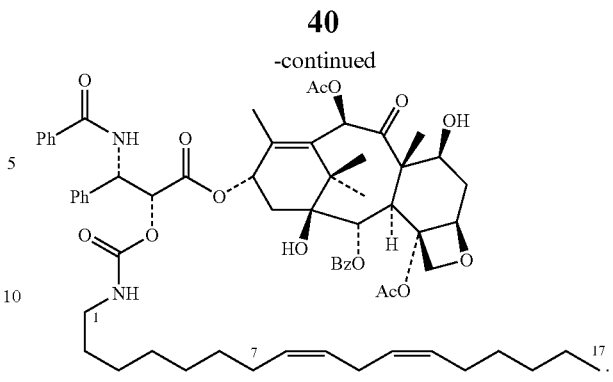

Paclitaxel, 2'-linoleyl carbamate ($C_{17}$)

Example 2

Preparation of N-methyl Fatty Amine Conjugates

The conjugates may be prepared with N-methyl group at the amino moiety of the fatty amine as shown below:

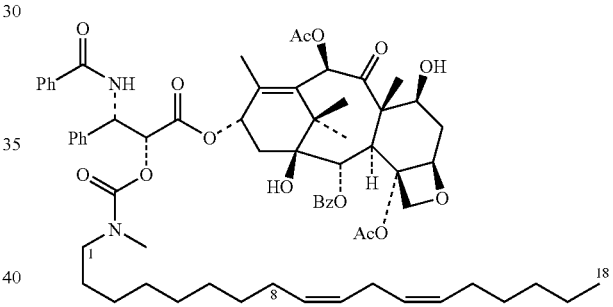

to prevent internal self-immolative destruction. N-methylated fatty amines may be prepared from fatty acids using the procedures described in the Examples and described generally (in Yamada, F., et al. Heterocycles 1986, 24, 1223 and Somei, M., et al. Heterocycles 1987, 26, 895., both hereby incorporated by reference).

Example 3

Synthesis of a Fatty Amine-adefovir Conjugate Via a Urea Linkage

Adefovir (PMEA) was conjugated to a fatty amine using the following procedures:

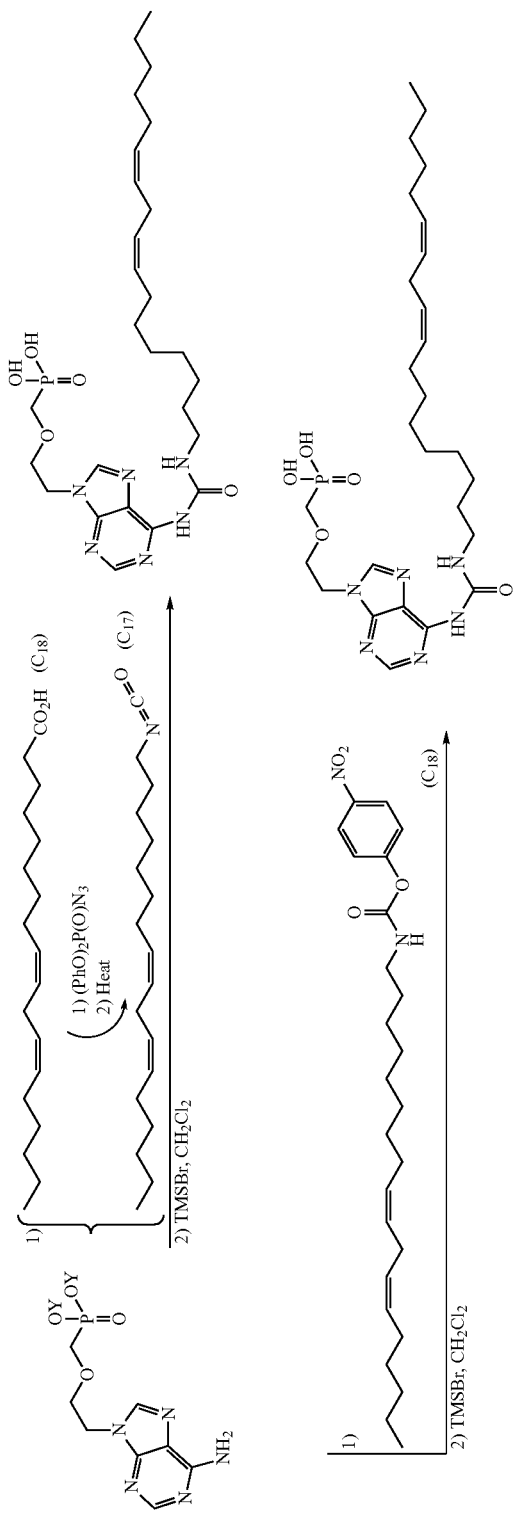

wherein Y is methyl or ethyl, (PhO)$_2$P(O)N$_3$ is diphenylphosphoryl azide, and TMSBr is bromotrimethylsilane. One skilled in the art will appreciate that the number of carbons in the fatty amine moiety of the conjugate is governed by both the starting material and synthetic method chosen.

Example 4

Synthesis of a Fatty Amine-vincristine Conjugate Via an Amide Linkage

Vincristine is conjugated to a fatty amine at position 23 at the methyl ester using the following procedure:

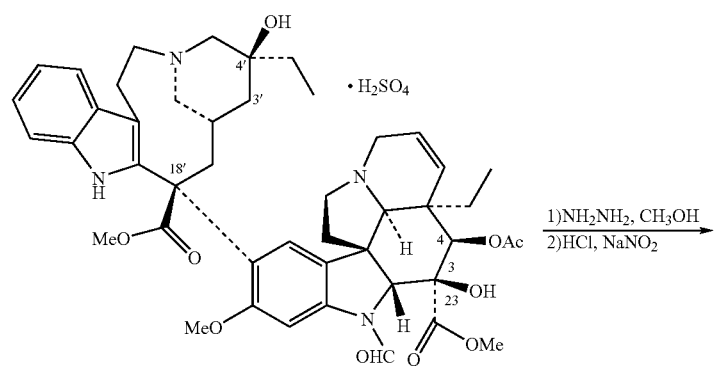

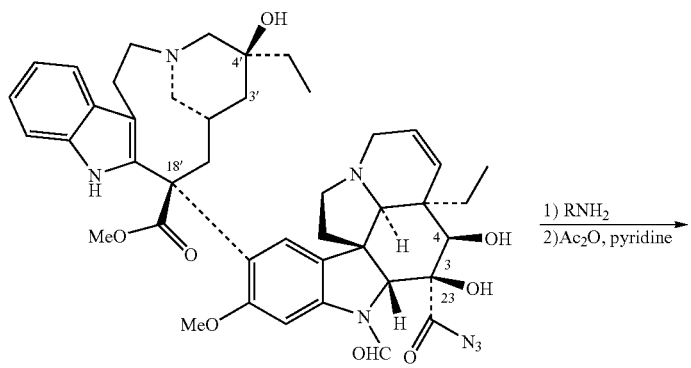

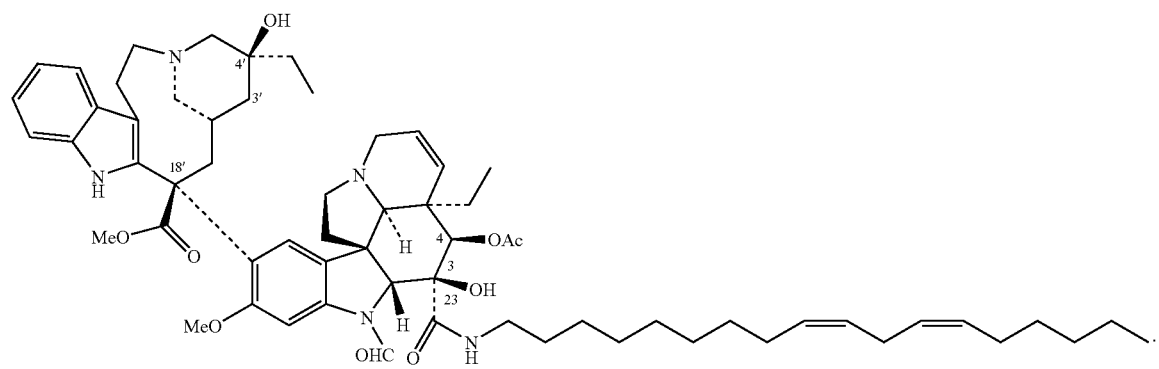

One skilled in the art will appreciate that vinblastine is conjugated to a fatty amine using the same procedure.

Example 5

Synthesis of a Fatty Amine-vincristine Conjugate Via a Carbamate Linkage

Vincristine is conjugated to a fatty amine at position 4 using the following procedure:

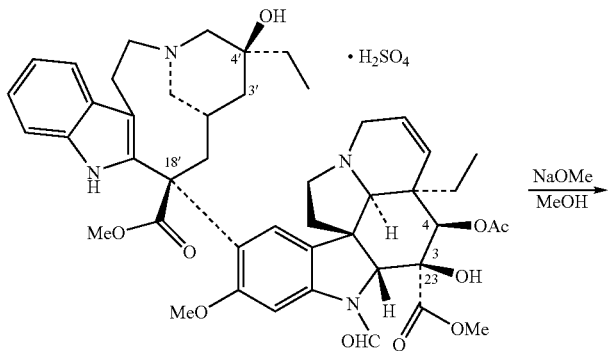

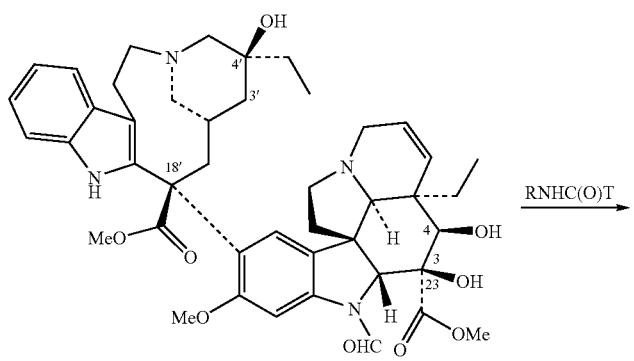

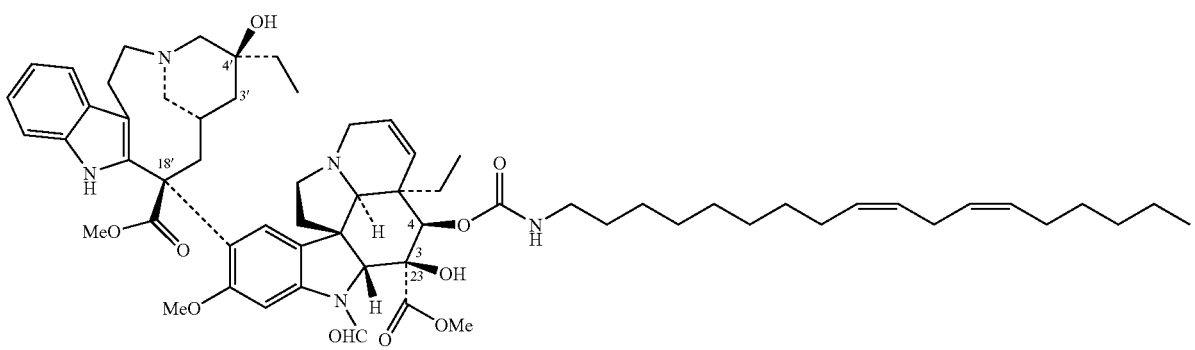

wherein RNHC(O)T is a fatty amine activated with a leaving group. The following fatty amine-vincristine conjugate with a thionocarbamate linker is prepared following an analogous procedure:

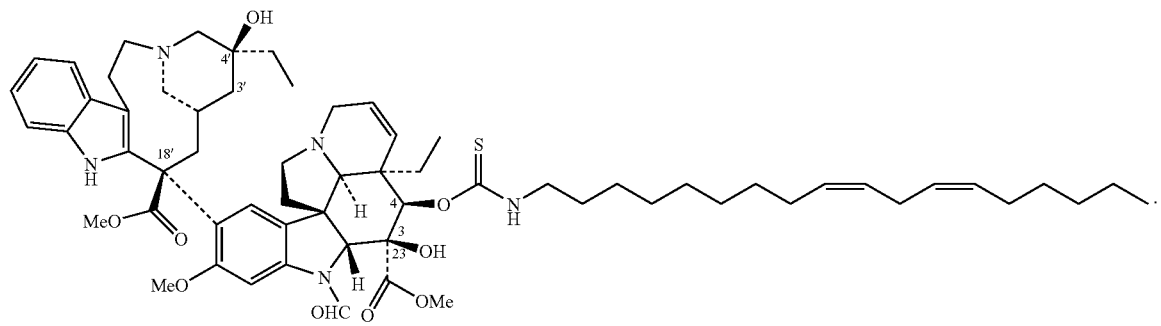

15

One skilled in the art will appreciate that vinblastine is conjugated to fatty amines using the same procedures.

Example 6

Synthesis of a Fatty Amine Pharmaceutical Agent Conjugate Via a Urea Linkage

An isocyanate was prepared from a fatty acid (equivalent to an activated fatty amine) and then conjugated to a pharmaceutical agent (XNH$_2$) using the following procedure:

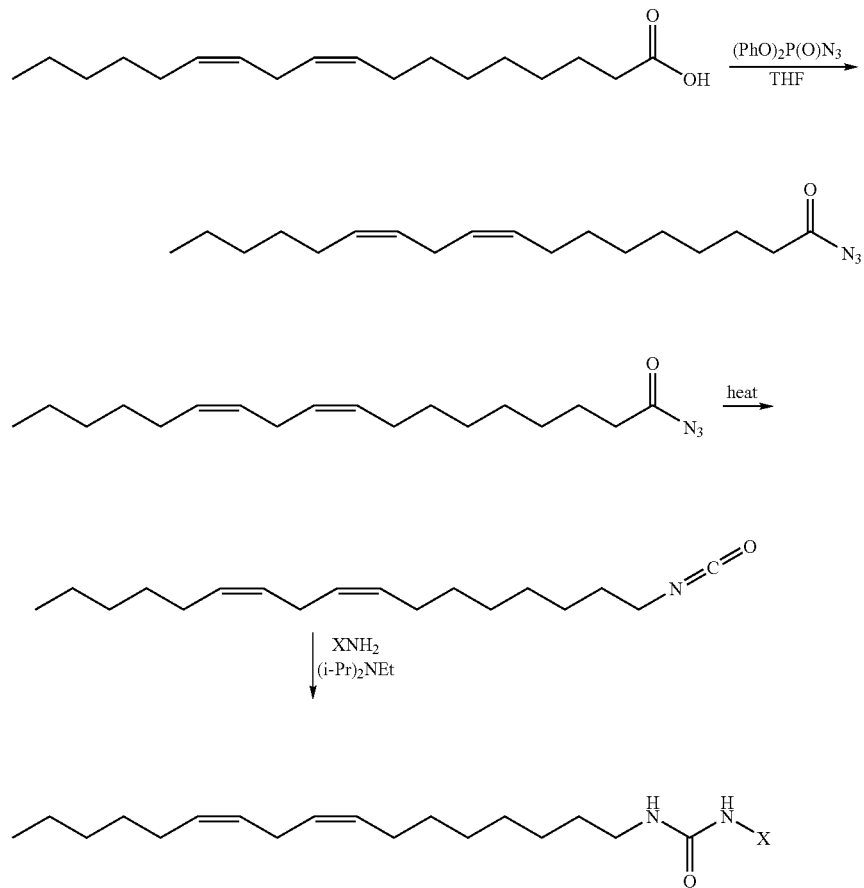

wherein (PhO)$_2$P(O)N$_3$ is diphenylphosphoryl azide. This process was generally used to produce conjugates with an odd number of carbon atoms in the fatty amine moiety.

Example 7

Synthesis of Fatty Amine Pharmaceutical Agent Conjugate Via a Urea Linkage

The fatty amine was conjugated to a pharmaceutical agent (XNH$_2$) using the following procedure:

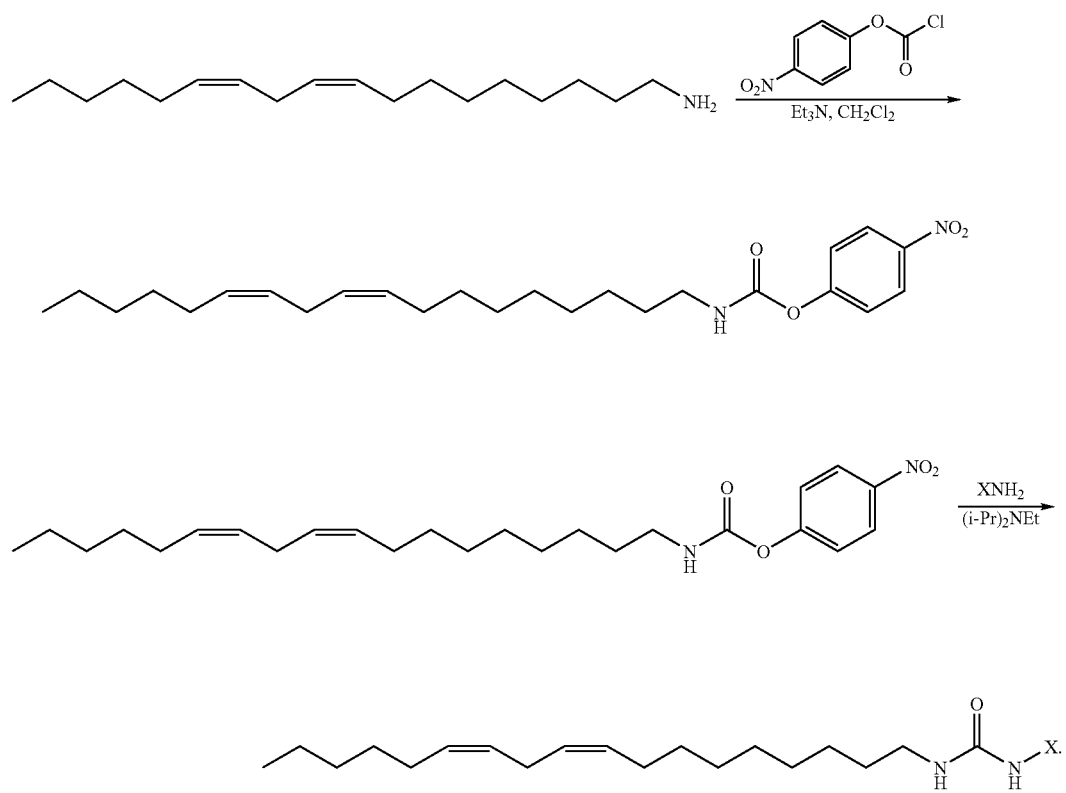

This process was generally used to produce conjugates with an even number of carbon atoms in the fatty amine moiety.

Example 8

Synthesis of a Fatty Amine Pharmaceutical Agent Conjugate Via a Guanidine Linkage Fatty amines are conjugated to doxorubicin using the following procedure:

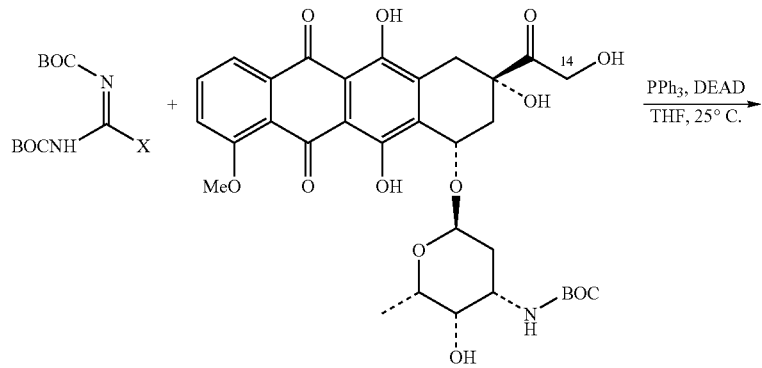

51
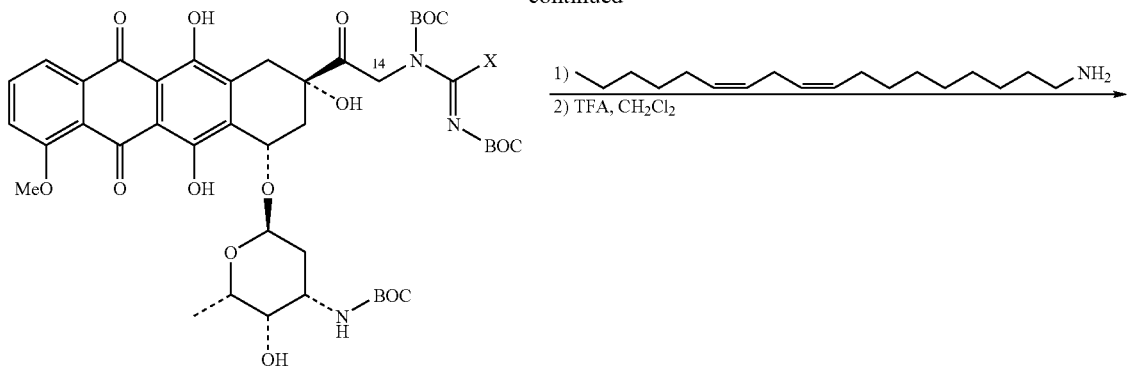
-continued
52
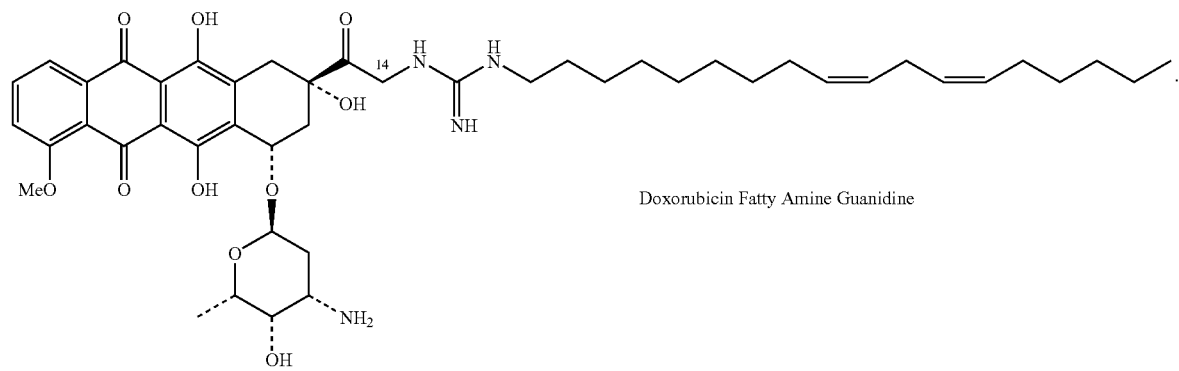
Doxorubicin Fatty Amine Guanidine
wherein
X = SMe  (1, 3-Bis(tert-butoxycarbonyl)-2-methyl-2-thiopseudourea) or
X = [pyrazole structure]  (N, N'-Bis(tert-butoxycarbonyl)-1H-pyrazole-1-carboxamidine)

Example 9
Examples of Etoposide Conjugates
The following etoposide-fatty amine conjugates are prepared using analogous methods to those described above and in the specification:
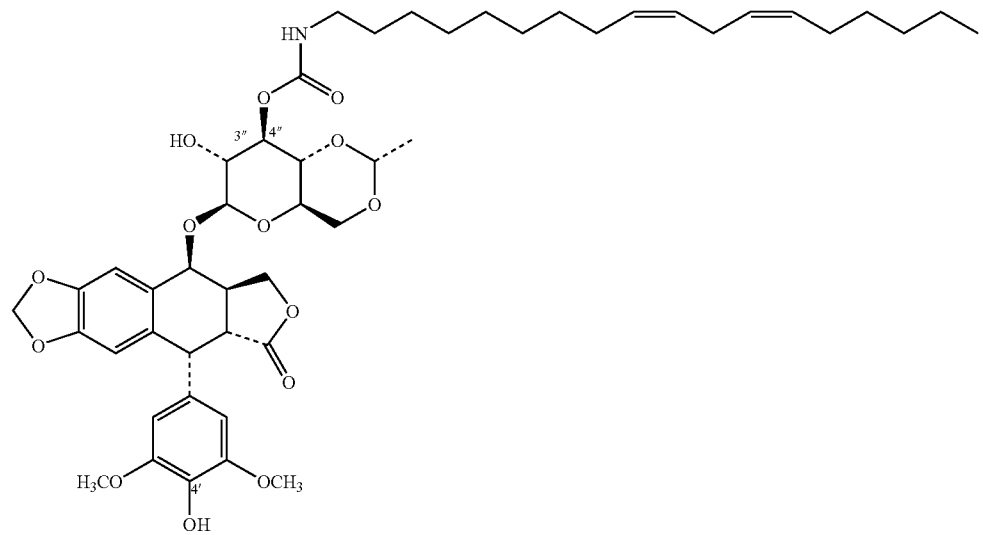
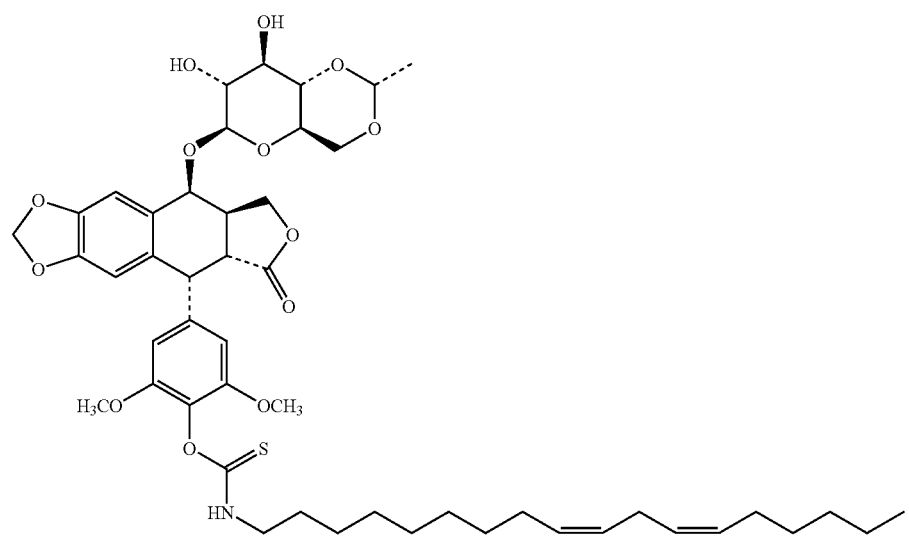

-continued
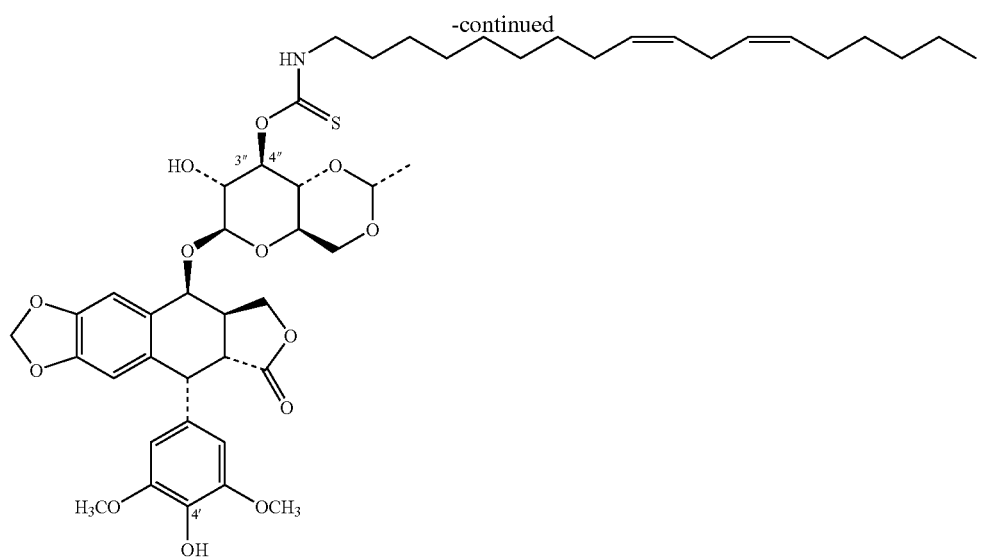
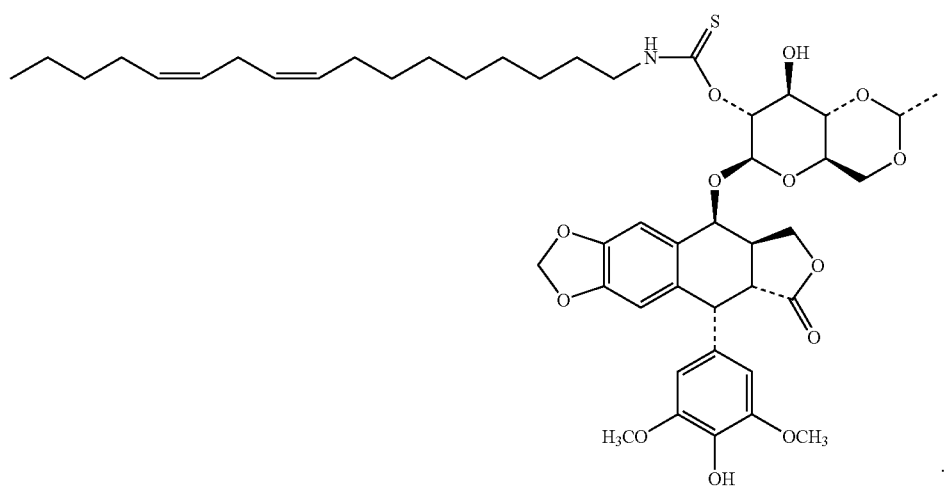
Example 10
Examples of Clozapine Conjugates
The following clozapine-fatty amine conjugates are prepared using analogous methods to those described above and in the specification:
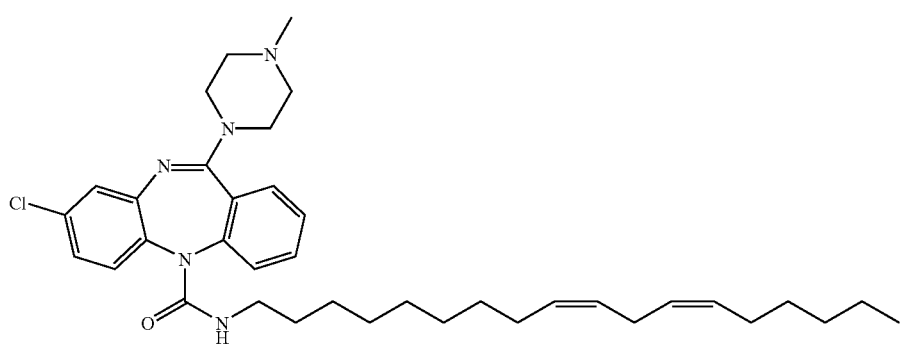

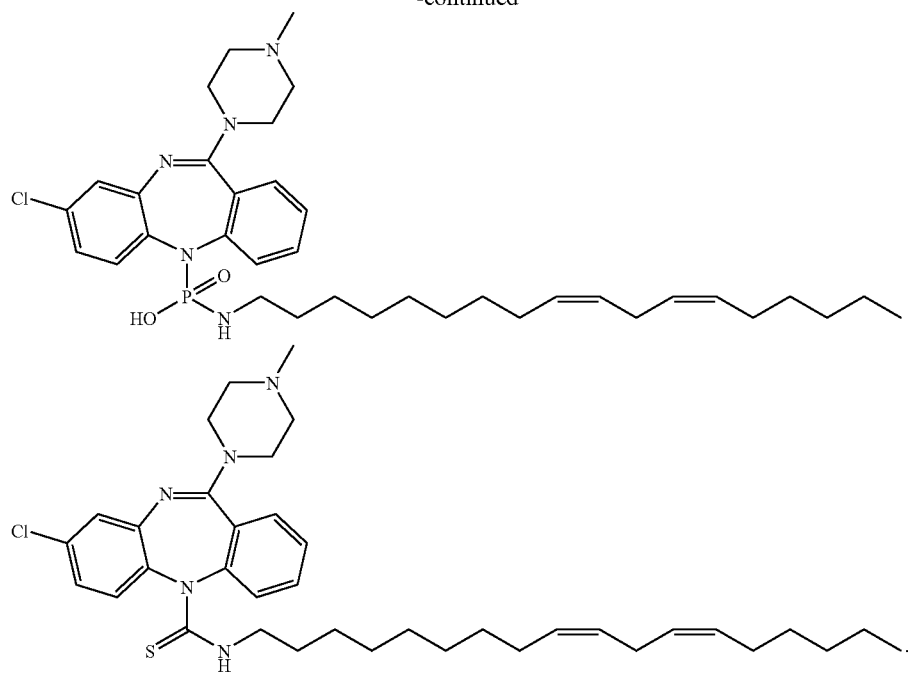
Example 11
Examples of Gemcitabine Conjugates
The following gemcitabine-fatty amine conjugates are prepared using analogous methods to those described above and in the specification:
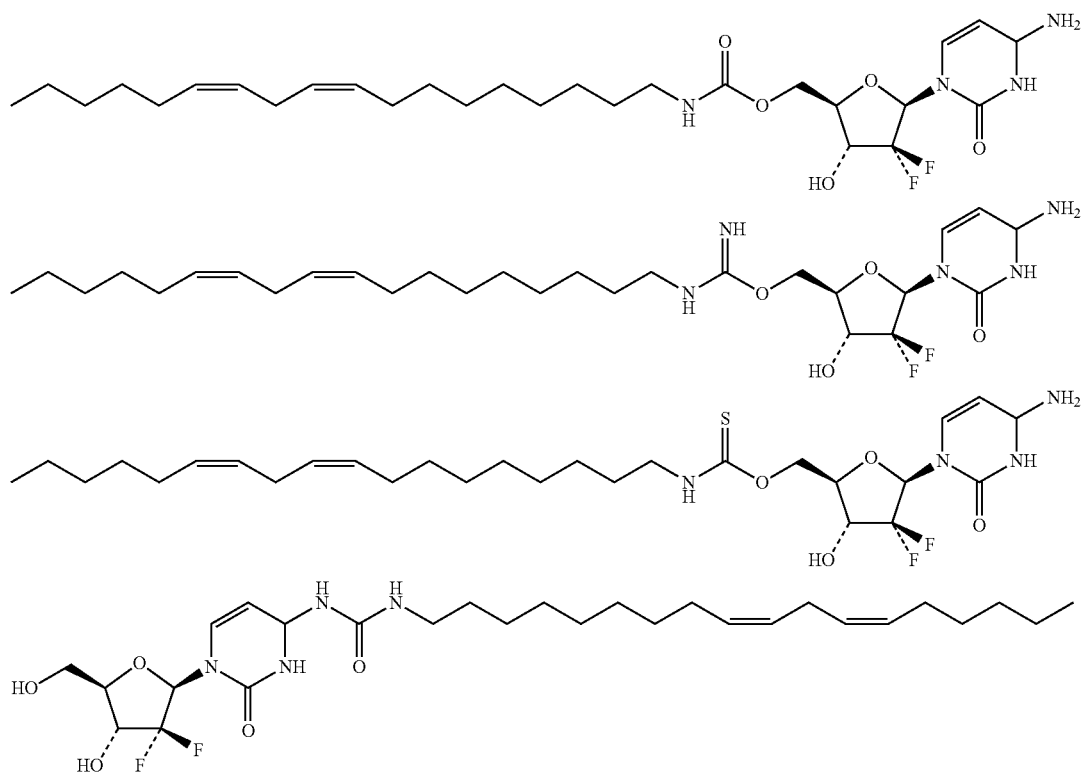

-continued

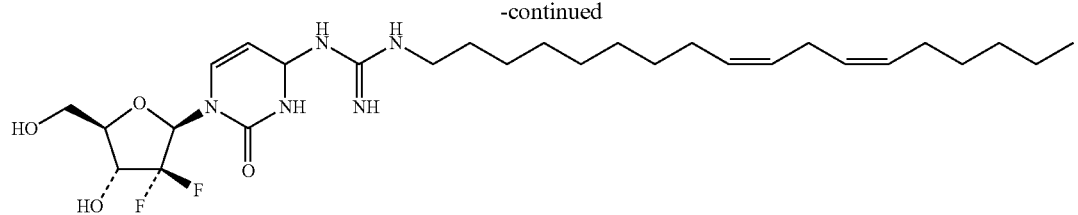

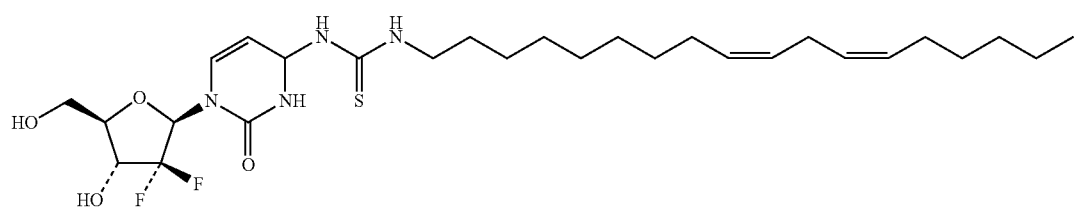

Example 12

Examples of Flavopiridol Conjugates

The following flavopiridol-fatty amine conjugates are prepared using analogous methods to those described above and in the specification:

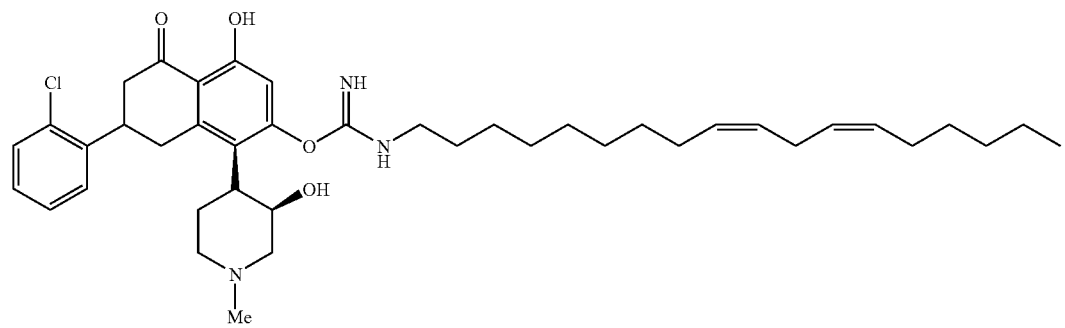

Flavopiridol, 7-linoleyl amine isourea

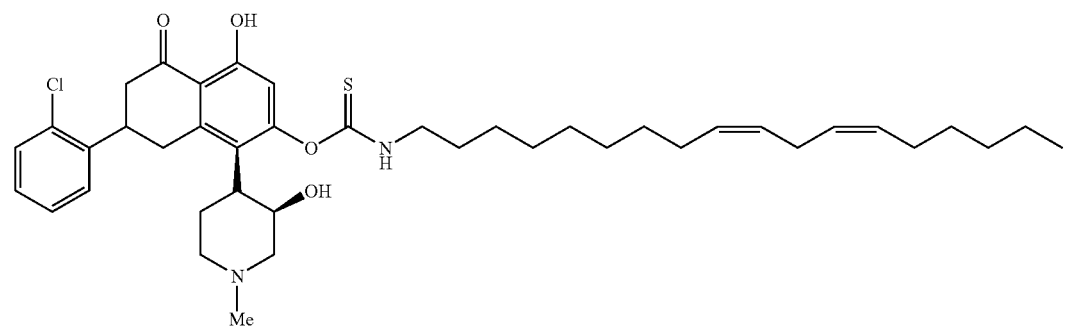

Flavopiridol, 7-linoleyl thionocarbamate

Similarly, conjugates are prepared with fatty amines conjugated at the 5 position and at the 3 position of flavopiridol.

Example 13

Examples of Purvalanol Conjugates

The following purvalanol B-fatty amine conjugates were prepared using analogous methods to those described above and in the specification:

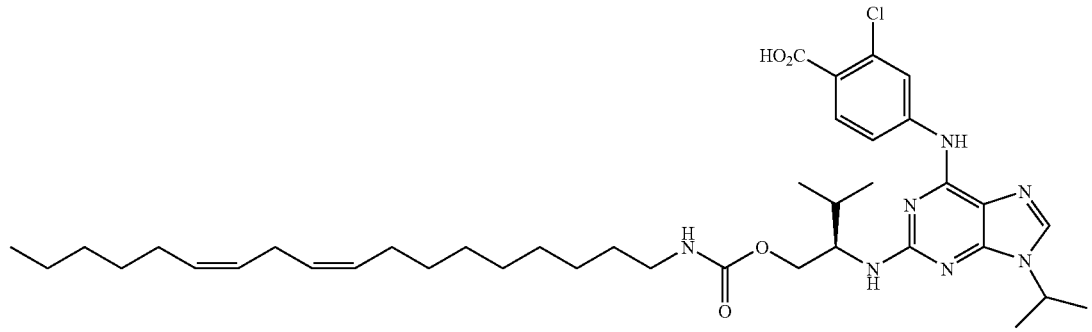

Purvalanol B, linoleyl carbamate

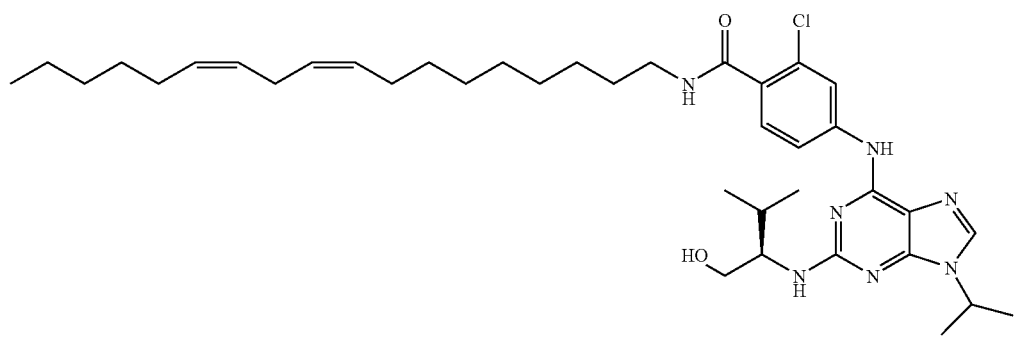

Purvalanol B, linoleyl amide

Conjugation at the carboxylic acid moiety of Purvalanol A requires protection of the free hydroxyl group, which may be routinely accomplished by those skilled in the art. One skilled in the art will also appreciate that fatty amines may also be conjugated to an amino group of purvalanol A as well as that the analogous types of fatty amine conjugates may be formed with purvalanol B.

Example 14

Examples of Roscovitine Conjugates

The following roscovitine-fatty amine conjugates are prepared using analogous methods to those described above and in the specification:

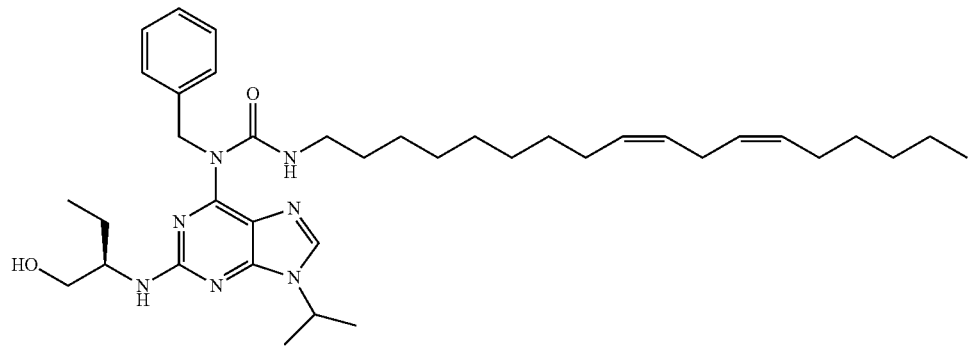

Roscovitine, 6-linoleyl urea ($C_{18}$)

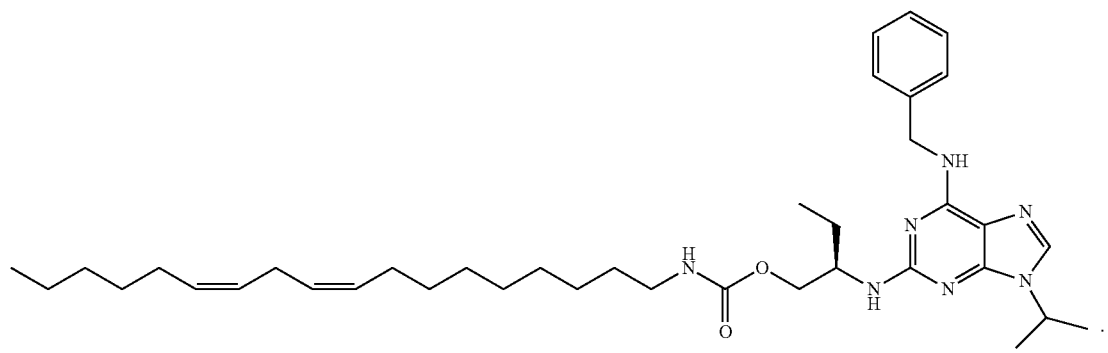

Roscovitine, 3'-linoleyl carbamate ($C_{18}$)

Similarly, conjugates are prepared with fatty amines either conjugated to the 1' guanidinium amine nitrogen or the C6 benzyl amine nitrogen in after protecting the primary hydroxyl group of roscovitine.

Example 15

Synthesis of Fatty Amines with Even-numbered Carbon Chains

Fatty alcohols having even-numbered carbon chains are typically obtained from naturally occurring fatty acids via reduction, and serve as a good source of fatty amines having even-numbered carbon chains. Thus, treatment of an even-numbered carbon chain fatty alcohol with phthalimide under Mitsonubu conditions (PPh3, DEAD, THF) provides the corresponding N-fatty alkyl phthalimide. Hydrazinolysis of the N-fatty alkyl phthalimide intermediate with hydrazine or methylhydrazine provides the desired fatty amine having an even-numbered carbon chain as shown:

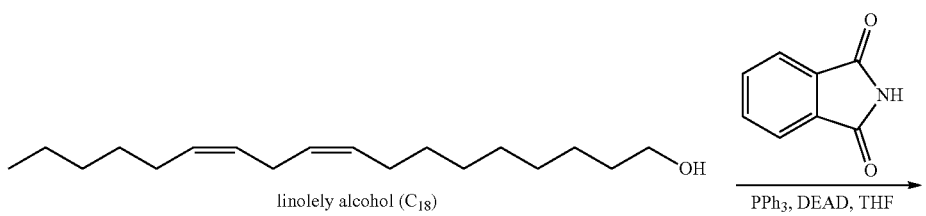

linolely alcohol ($C_{18}$)    PPh3, DEAD, THF

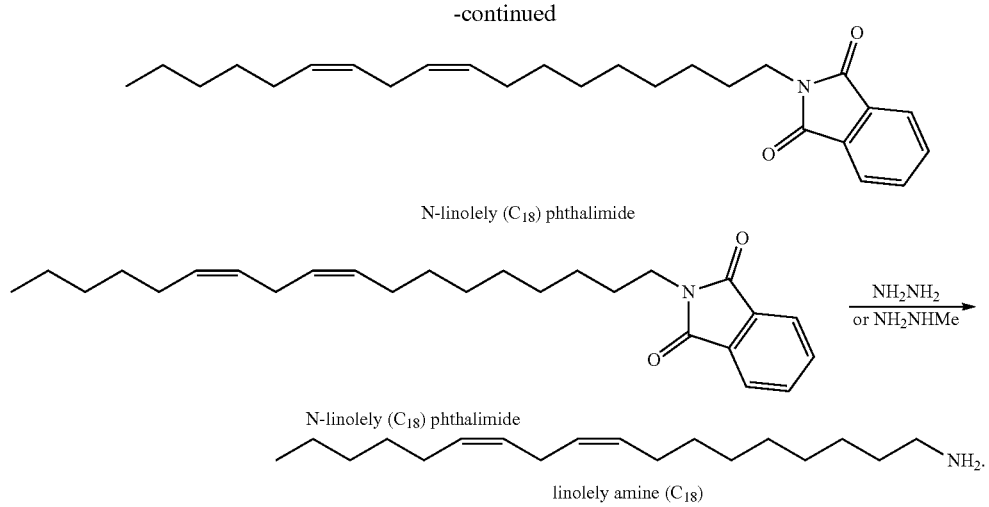

N-linolely (C$_{18}$) phthalimide linolely amine (C$_{18}$)

Example 16

Synthesis of Fatty Amines with Odd-numbered Carbon Chains

Fatty acids having even-numbered carbon chains, when treated with diphenyl phosphoryl azide in THF at room temperature, are converted into the corresponding fatty acyl azide. Curtius rearrangement of the fatty acyl azide intermediate to the corresponding fatty isocyanate is accomplished by careful heating. The fatty isocyanate intermediate (equivalent to an activated odd-numbered carbon chain fatty amine) is coupled directly to a pharmaceutical agent possessing either a hydroxyl or amino group, without isolation and purification, as shown:

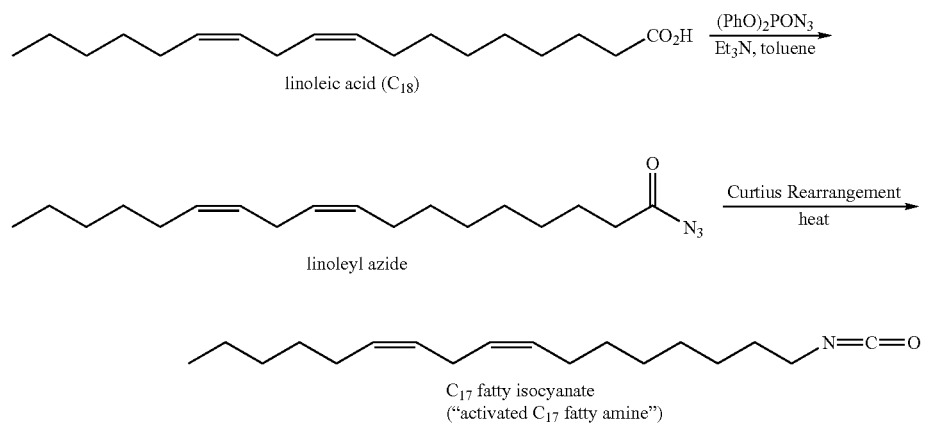

Example 17

N-Methylation of Even-numbered Carbon Chain Fatty Amines

The even-numbered carbon chain fatty amine (synthesized as described above) are treated with methyl chloroformate, thus providing the corresponding methyl carbamate. Reduction of the methyl carbamate using lithium aluminum hydride provides the desired N-methylated fatty amine having an even-numbered carbon chain, as shown:

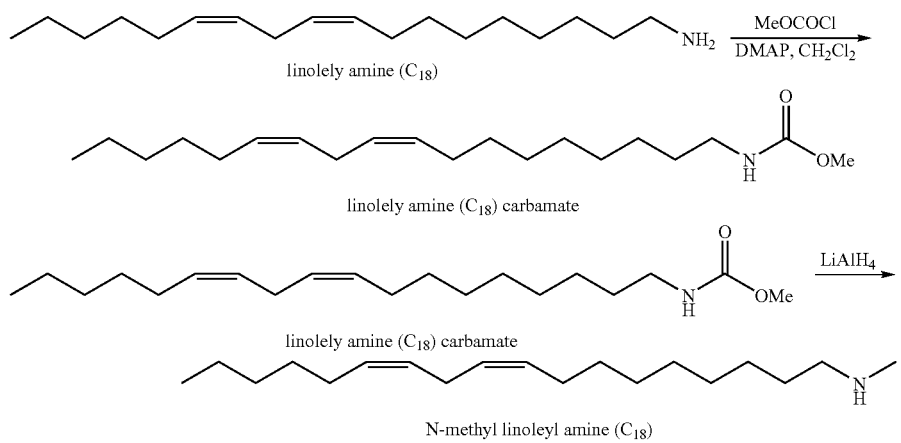

Example 18

N-Methylation of Odd-numbered Carbon Chain Fatty Amines

The fatty isocyanate (synthesized as described above) is treated with methanol, thus providing the corresponding methyl carbamate. Reduction of the methyl carbamate using lithium aluminum hydride provides the desired N-methylated fatty amine having an odd-numbered carbon chain, as shown:

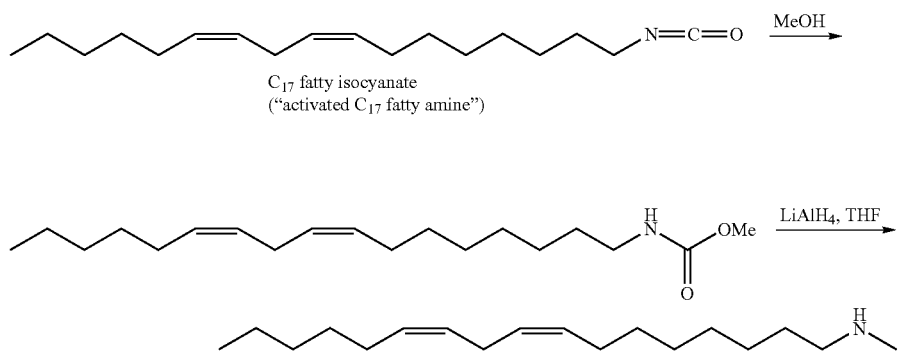

Example 19

Examples of Adefovir Conjugates

The following adefovir-fatty amine conjugates were prepared using analogous methods to those described above and in the specification:

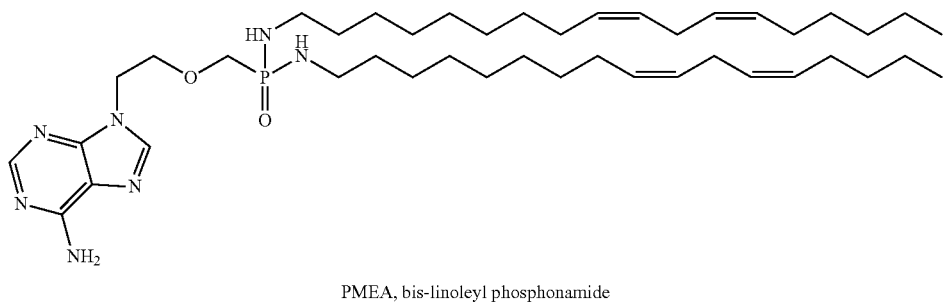

PMEA, bis-linoleyl phosphonamide

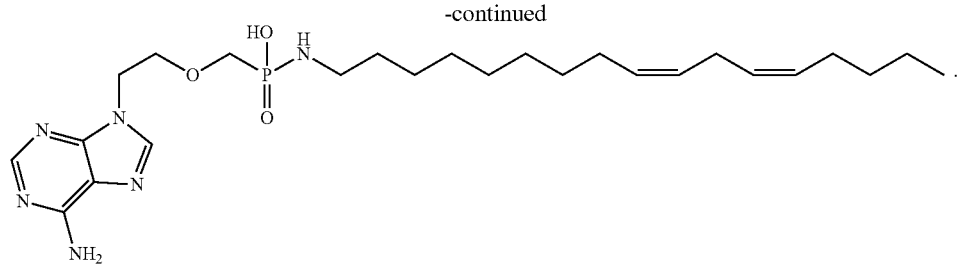
PMEA, linoleyl phosphonamide
Example 20
Synthesis of a Fatty Amine-SN-38 Conjugate Via a Carbamate Linkage
SN-38 is conjugated to a fatty amine at position 20 using the following procedure:
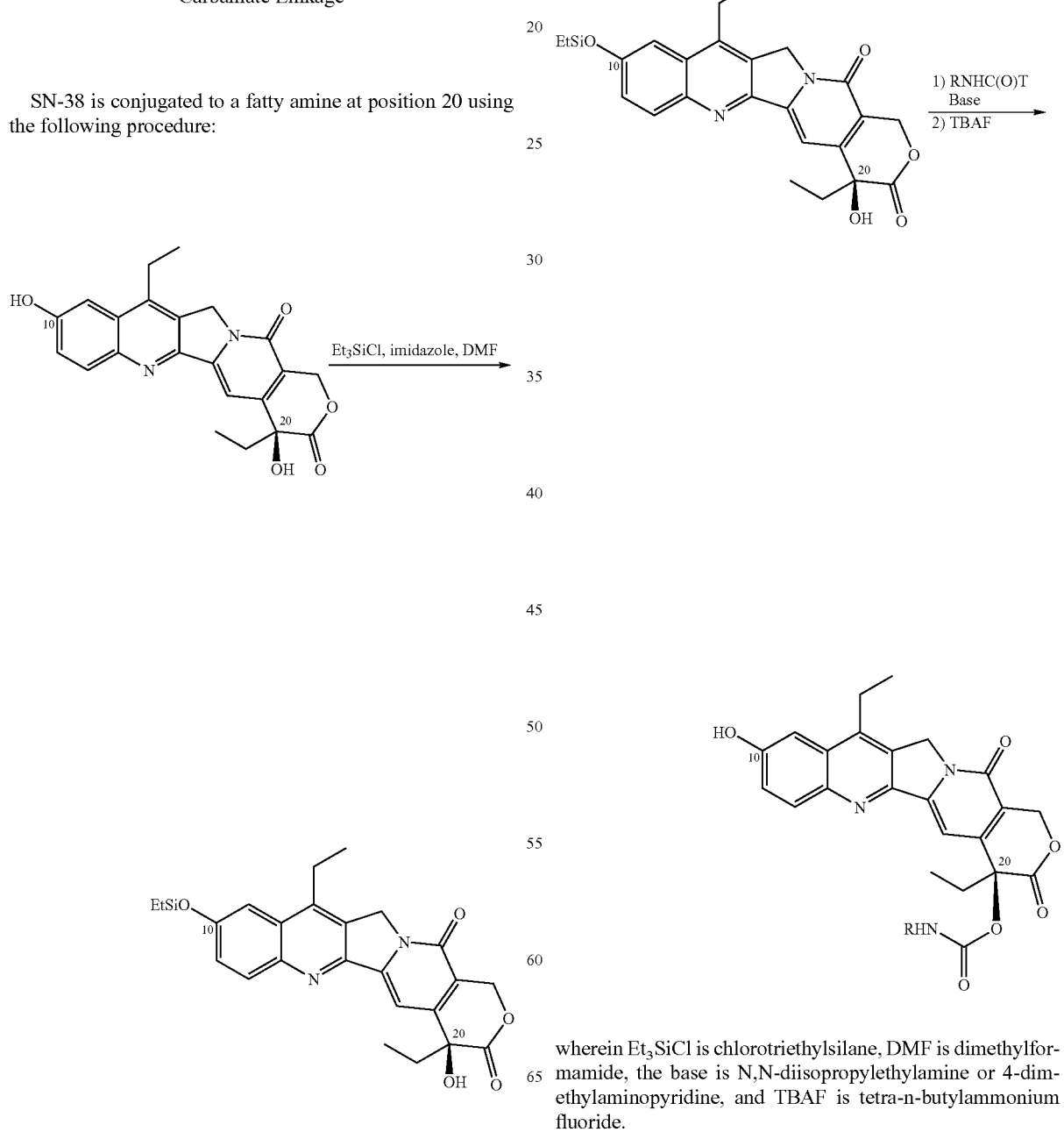
wherein Et₃SiCl is chlorotriethylsilane, DMF is dimethylformamide, the base is N,N-diisopropylethylamine or 4-dimethylaminopyridine, and TBAF is tetra-n-butylammonium fluoride.

71 72
Example 21
Example of SN-38 Conjugates
The following SN-38-fatty amine conjugates are prepared using analogous methods to those described above and in the specification:
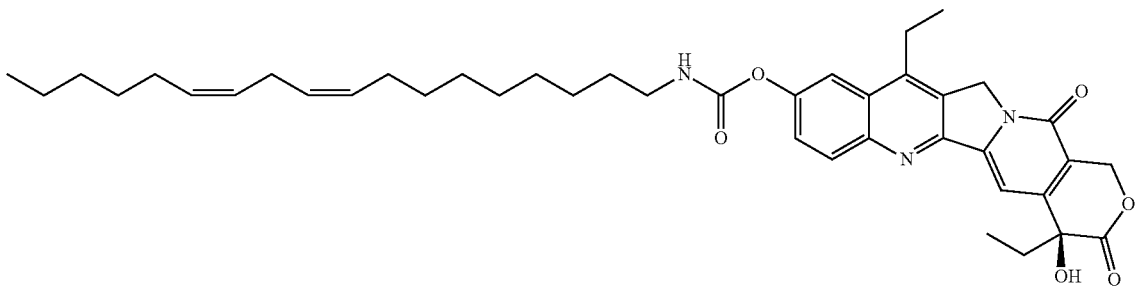
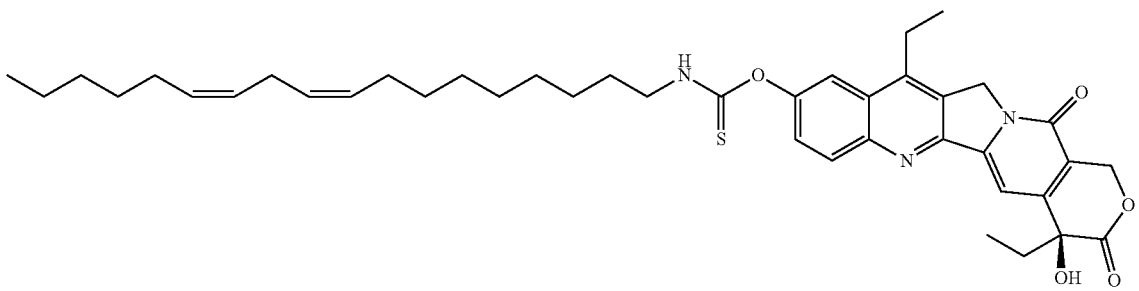
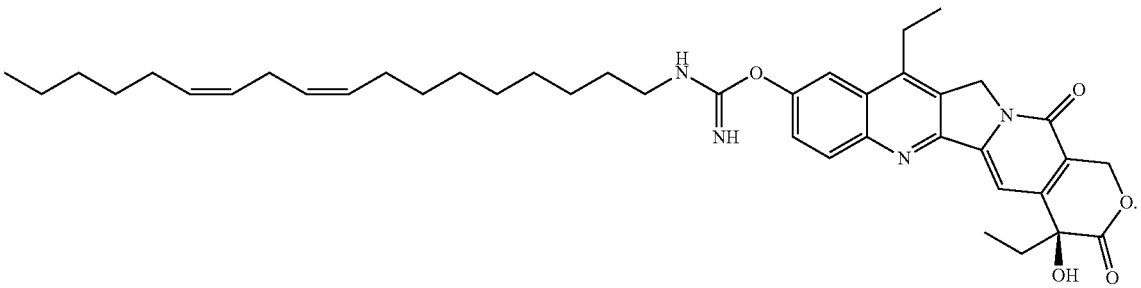
Example 22
Synthesis of a Fatty Amine-adefovir Conjugate Via a Phosphonamide Linkage
Adefovir is conjugated to a fatty amine at using the following procedure:
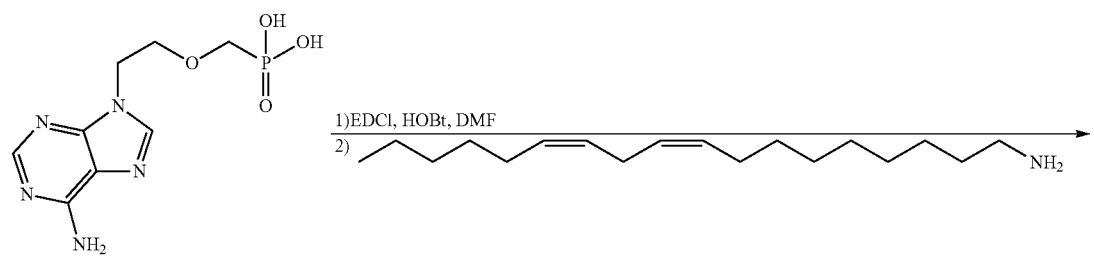

-continued

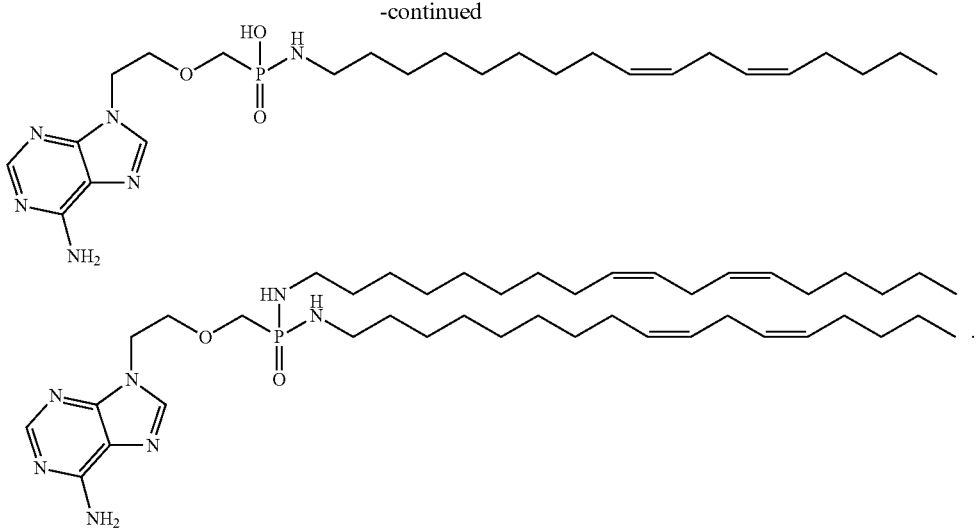

As one skilled in the art will recognize, one equivalent of linoleyl amine will generally form a conjugate with one fatty amine moiety and two equivalents of linoleyl amine will generally form a conjugate with two fatty amine moieties.

What is claimed is:

1. A compound of the formula:

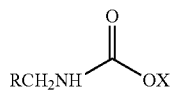

wherein R is a $C_8$-$C_{26}$ fatty group of a fatty acid R—$CO_2H$ and X is an anticancer agent moiety of an anticancer agent XOH, wherein the anticancer agent is paclitaxel.

2. The compound of claim 1, wherein the fatty acid is selected from the group consisting of octanoic (caprylic); nonanoic (pelargonic); decanoic (capric); undecanoic (hendecanoic); dodecanoic (lauric); tridecanoic; tetradecanoic (myristic); pentadecanoic; hexadecanoic (pamitic); heptadecanoic (margaric); octadecanoic (stearic); 12-hydroxy stearic; nonadecanoic; eicosanoie (arachidic); heneicosanoic; docosanoic (behenic); tricosanoic; tetracosanoic (lignoceric); 10-undecenoic (hendecenoic); 11-dodecenoic; 12-tridecenoic; 9-tetradecenoic (myristoleic); 9-trans-tetradecenoic (myristelaidic); 10-pentadecenoic; 10-trans-pentadecenoic; 9-hexadecenoic (palmitoleic); 8-trans-hexadecenoic (palmitelaidic); 10-heptadecenoic; 10-trans-heptadecenoic; 6-octadecenoic (petroselinic); 6-trans-octadecenoic (petroselaidic); 8-octadecenoic (oleic); 9-11-octadecenoic (vaccenic); 11-trans-octadecenoic (transvaccenic); 9-cis-12 hydroxy-octadecenoic (ricinoleic); 9-trans-12-hydroxy-octadecenoic (ricinelaidic); 7-nonadecenoic; 7-trans-nonadecenoic; 10-nonadecenoic; 10-trans-nonadecenoic; 10-13 -nonadecadienoic; 10-13-trans-nonadecadienoic; 8-12-octadecadienoic (linoleic); 9-trans-12-trans octadecadienoic (linoelaidic); octadecadienoic (conjugated); 9-12-15-octadecatrienoic (linolenic); 6-9-12-octadecatrienoic (gamma linolenic); 11-trans-eicosenoic; 8eicosenoic; 11-eicosenoic; 5-eicosenoic; 11-14-eicosadienoic; 8-11-14-eicosatrienoic (homogamma linolenic); 11-14-17-eicosatrienoic; 5-8-11-14-eicosatetraenoic (arachidonic); 5-8-11-14-17-eicosapentaenoic; 7-10-13-16-19-docosapentaenoic; arachidonic; 13-docosenoic (erucic); 13-transdocosenoic (brassidic); 13-16-docosadienoic; 13-16-19-docosatrienoic; 7-10-13-16-docosatetraenoic- ; 4-7-10-13-16-19-docosahexaenoic (DHA); 12-heneicosenoic; 12-15-heneicosadienoic; 14-tricosenoic; and 15-tetracosenoic (nervonic).

3. The compound of claim 1, wherein the fatty acid is selected from myristic acid, palmitic acid, palmitoleic acid, stearic acid, oleic acid, vaccenic acid, linoleic acid, linolenic acid, arachidonic acid, eicosapentaenoic acid, docosenoic acid, docosatetraenoic acid, docosapentaenoic acid, docosahexaenoic acid, and nervonic acid.

4. The compound of claim 1, wherein the fatty acid is selected from the group of acids consisting of dodecanoic (lauric); tridecanoic; tetradecanoic (myristic); pentadecanoic; hexadecanoic (pamitic); heptadecanoic (margaric); octadecanoic (stearic); 12-hydroxy stearic; nonadecanoic; eicosanoic (arachidic); heneicosanoic; docosanoic (behenic); tricosanoic; tetracosanoic (lignoceric); 10-undecenoic (hendecenoic); 11-dodecenoic; 12-tridecenoic; 9-tetradecenoic (myristoleic); 9-trans-tetradecenoic (myristelaidic); 10-pentadecenoic; 10-trans-pentadecenoic; 9-hexadecenoic (palmitoleic); 8-trans-hexadecenoic (palmitelaidic); 10-heptadecenoic; 10-trans-heptadecenoic; 6-octadecenoic (petroselinic); 6-trans-octadecenoic (petroselaidic); 8-octadecenoic (oleic); 9-11-octadecenoic (vaccenic); 11-trans-octadecenoic (transvaccenic); 9-cis-12 hydroxy-octadecenoic (ricinoleic); 9-trans-12-hydroxy-octadecenoic (ricinelaidic); 7-nonadecenoic; 7-trans-nonadecenoic; 10-nonadecenoic; 10-trans-nonadecenoic; 10-13-nonadecadienoic; 10-13-trans-nonadecadienoic; 8-12-octadecadienoic (linoleic); 9-trans-12-trans octadecadienoic (linoelaidic); octadecadienoic (conjugated); 9-12-15-octadecatrienoic (linolenic); 6-9-12-octadecatrienoic (gamma linolenic); 11-trans-eicosenoic; 8-eicosenoic; 11-eicosenoic; 5-eicosenoic; 11-14-eicosadienoic; 8-11-14-eicosatrienoic (homogamma linolenic); 11-14-17-eicosatrienoic; 5-8-11-14-eicosatetraenoic (arachidonic); 5-8-11-14-17-eicosapentaenoic; 7-10-13-16-19-docosapentaenoic; arachidonic; 13-docosenoic (erucic); 13-transdocosenoic (brassidic); 13-16-docosadienoic; 13-16-19-docosatrienoic; 7-10-13-16-docosatetraenoic- ; 4-7-10-13-16-19-docosahexaenoic (DHA); 12-heneicosenoic; 12-15-heneicosadienoic; 14-tricosenoic; and 15-tetracosenoic (nervonic).

5. The compound of claim 1, wherein the fatty acid is selected from the group of acids consisting of tetradecanoic (myristic); pentadecanoic; hexadecanoic (pamitic); heptadecanoic (margaric); octadecanoic (stearic); 12-hydroxy stearic; nonadecanoic; eicosanoic (arachidic); heneicosanoic; docosanoic (behenic); tricosanoic; tetracosanoic (lignoceric); 10-undecenoic (hendecenoic); 11-dodecenoic; 12-tridecenoic; 9-tetradecenoic (myristoleic); 9-trans-tetradecenoic (myristelaidic); 10-pentadecenoic; 10-trans-pentadecenoic; 9-hexadecenoic (palmitoleic); 8-trans-hexadecenoic (palmitelaidic); 10-heptadecenoic; 10-trans-heptadecenoic; 6-octadecenoic (petroselinic); 6-trans-octadecenoic (petroselaidic); 8-octadecenoic (oleic); 9-11-octadecenoic (vaccenic); 11-trans-octadecenoic (transvaccenic); 9-cis-12 hydroxy-octadecenoic (ricinoleic); 9-trans-12-hydroxy-octadecenoic (ricinelaidic); 7-nonadecenoic; 7-trans-nonadecenoic; 10-nonadecenoic; 10-trans-nonadecenoic; 10-13-nonadecadienoic; 10-13-trans-nonadecadienoic; 8-12-octadecadienoic (linoleic); 9-trans-12-trans octadecadienoic (linoelaidic); octadecadienoic (conjugated); 9-12-15-octadecatrienoic (linolenic); 6-9-12-octadecatrienoic (gamma linolenic); 11-trans-eicosenoic; 8-eicosenoic; 11-eicosenoic; 5-eicosenoic; 11-14-eicosadienoic; 8-11-14-eicosatrienoic (homogamma linolenic); 11-14-17-eicosatrienoic; 5-8-11-14-eicosatetraenoic (arachidonic); 5-8-11-14-17-eicosapentaenoic; 7-10-13-16-19-docosapentaenoic; arachidonic; 13-docosenoic (erucic); 13-transdocosenoic (brassidic); 13-16-docosadienoic; 13-16-19-docosatrienoic; 7-10-13-16-docosatetraenoic- ; 4-7-10-13-16-19-docosahexaenoic (DHA); 12-heneicosenoic; 12-15-heneicosadienoic; 14-tricosenoic; and 15-tetracosenoic (nervonic).

6. A pharmaceutical preparation comprising a therapeutically effective amount of compound of the formula:

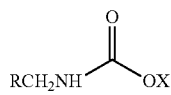

wherein R is a $C_8$-$C_{26}$ fatty group of a fatty acid R—$CO_2$H and X is an anticancer agent moiety of the anticancer agent XOH, and a pharmaceutically acceptable carrier, wherein the anticancer agent is paclitaxel.

7. The pharmaceutical preparation of claim 6, wherein the fatty acid is selected from myristic acid, palmitic acid, palmitoleic acid, stearic acid, oleic acid, vaccenic acid, linoleic acid, linolenic acid, arachidonic acid, eicosapentaenoic acid, docosenoic acid, docosatetraenoic acid, docosapentaenoic acid, docosahexaenoic acid, and nervonic acid.

8. A method of making a compound of the formula:

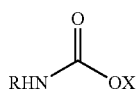

comprising reacting an intermediate of the formula R—N═C═O with an anticancer agent of the formula XOH for a time sufficient to form the compound;
wherein R is a $C_8$-$C_{26}$ fatty group of a fatty acid, R—$CO_2$H, and X is an anticancer agent moiety of the anticancer agent of the formula XOH, wherein the anticancer agent is paclitaxel.

9. The method of claim 8, wherein the fatty acid is selected from myristic acid, palmitic acid, palmitoleic acid, stearic acid, oleic acid, vaccenic acid, linoleic acid, linolenic acid, arachidonic acid, eicosapentaenoic acid, docosenoic acid, docosatetraenoic acid, docosapentaenoic acid, docosahexaenoic acid, and nervonic acid.

10. A compound of the formula:

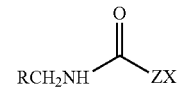

wherein R is a $C_8$-$C_{26}$ fatty group of a fatty acid R—$CO_2$H and X is an anticancer agent moiety of an anticancer agent XZH, wherein the anticancer agent is paclitaxel, Z is O, a primary amino group, or a secondary amino group.

11. The compound of claim 10, wherein fatty acid is selected from myristic acid, palmitic acid, palmitoleic acid, stearic acid, oleic acid, vaccenic acid, linoleic acid, linolenic acid, arachidonic acid, eicosapentaenoic acid, docosenoic acid, docosatetraenoic acid, docosapentaenoic acid, docosahexaenoic acid, and nervonic acid.

12. A pharmaceutical preparation comprising a therapeutically effective amount of compound of the formula:

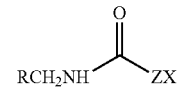

wherein R is a $C_8$-$C_{26}$ fatty group of a fatty acid R—$CO_2$H and X is an anticancer agent moiety of an anticancer agent XZH and a pharmaceutically acceptable carrier, wherein the anticancer agent is paclitaxel, and Z is O, a primary amino group, or a secondary amino group.

13. The pharmaceutical preparation of claim 12, wherein the fatty acid is selected from myristic acid, palmitic acid, palmitoleic acid, stearic acid, oleic acid, vaccenic acid, linoleic acid, linolenic acid, arachidonic acid, eicosapentaenoic acid, docosenoic acid, docosatetraenoic acid, docosapentaenoic acid, docosahexaenoic acid, and nervonic acid.

14. A method of making a compound of the formula:

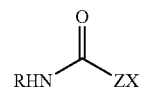

comprising reacting an intermediate of the formula R—N═C═O with an anticancer agent of the formula XZH for a time sufficient to form the compound;
wherein R is a $C_8$-$C_{26}$ fatty group of a fatty acid, R—$CO_2$H, X is an anticancer agent moiety of the anticancer agent of the formula XZH, wherein the anticancer agent is paclitaxel, and Z is O, a primary amino group, or a secondary amino group.

15. The method of claim 14, wherein the fatty acid is selected from myristic acid, palmitic acid, palmitoleic acid, stearic acid, oleic acid, vaccenic acid, linoleic acid, linolenic acid, arachidonic acid, eicosapentaenoic acid, docosenoic acid, docosatetraenoic acid, docosapentaenoic acid, docosahexaenoic acid, and nervonic acid.

* * * * *

UNITED STATES PATENT AND TRADEMARK OFFICE
CERTIFICATE OF CORRECTION

PATENT NO. : 8,552,054 B2
APPLICATION NO. : 10/108255
DATED : October 8, 2013
INVENTOR(S) : Charles S. Swindell Page 1 of 1

It is certified that error appears in the above-identified patent and that said Letters Patent is hereby corrected as shown below:

In the Claims:

At column 73, claim 2, line 46, delete "eicosanoie" and insert --eicosanoic--

At column 73, claim 2, line 64, delete "8eicosenoic" and insert --8-eicosenoic--

Signed and Sealed this
Thirty-first Day of December, 2013

Margaret A. Focarino
*Commissioner for Patents of the United States Patent and Trademark Office*